United States Patent [19]
Smith et al.

[11] Patent Number: 5,311,764
[45] Date of Patent: May 17, 1994

[54] REBOUND HAMMER

[75] Inventors: Anthony Smith, Oxnard; Dan Goff, Ventura; Roman Kruchowy, Somis; Carl Rhoads, Ventura, all of Calif.

[73] Assignee: The United States of America as represented by the Secretary of the Navy, Washington, D.C.

[21] Appl. No.: 94,662

[22] Filed: Jul. 19, 1993

Related U.S. Application Data

[63] Continuation-in-part of Ser. No. 860,743, Mar. 25, 1992.

[51] Int. Cl.$^5$ .............................................. G01L 5/00
[52] U.S. Cl. .................................. 73/12.04; 73/12.01
[58] Field of Search ................... 73/11, 12, 79, 81, 82, 73/83, 84, 85, 12.04, 12.01

Primary Examiner—Richard E. Chilcot, Jr.
Assistant Examiner—R. Biegel

[57] ABSTRACT

A measuring apparatus which detects defects in underwater concrete structures by measuring the compressive strength of the structure. The measuring apparatus comprises a rebound hammer which has extending from the nose thereof a plunger. The plunger is pressed against the structure whose compressive strength is being measured forcing the plunger into the rebound hammer's housing which releases a spring driven mass. A resistive film strip which is in electrical contact with the mass detects the maximum rebound of the mass and provides an electrical signal indicative of this maximum rebound. A data acquisition and processing circuit comprising a microprocessor and signal conditioning electronics receives, processes and stores the electrical signals provided by the resistive strip. This circuit includes a peak detection circuit which captures the peak output signal from the resistive strip. The peak detection circuit then interrupts the microprocessor and sends an analog signal proportional to the maximum rebound of the mass to an analog to digital converter which converts the analog signal to a digital data for processing by the microprocessor. The microprocessor then calculates the compressive strength of the underwater concrete structure under test.

18 Claims, 7 Drawing Sheets

REBOUND HAMMER

This application is a continuation-in-part of U.S. patent application Ser. No. 07/860,743 filed Mar. 25, 1992, now abandoned.

BACKGROUND OF THE INVENTION

1. Field of the Invention

The present invention relates generally to apparatus for measuring the strength of concrete structures and, in particular, to a rebound hammer which measures the compressive strength of underwater concrete structures such as piers, retaining walls and the like.

2. Description of the Prior Art

Naval concrete underwater structures include piers, retaining walls, easements and the like. Over time fresh water and seawater will have an adverse effect on such underwater concrete structures in the form of wear and damage which necessitates inspection of the structures and if necessary repair or replacement of the structures.

In the past visual inspection of underwater concrete structures has been used to determine the condition of the structures. The qualitative data obtained from visual inspection is often inadequate to accurately assess the condition of the structure. In particular, a visual inspection of an underwater concrete structure will often fail to identify an internal defect within the structure.

A need therefore exist for a measuring apparatus which provides a long sought solution to the problem of accurately measuring internal damage and deterioration to underwater concrete structures such as piers, retaining walls, easements and the like.

SUMMARY OF THE INVENTION

The purpose of the present invention is to provide a measuring apparatus which accurately detects external and internal defects in underwater concrete structures such as piers, retaining walls, easements and the like by measuring the compressive strength of the structure. The measuring apparatus of the present invention comprises a rebound hammer which has extending from the nose thereof a plunger. The plunger is pressed against the underwater concrete structure whose compressive strength is being measured forcing the plunger into the rebound hammer's housing which releases a spring driven mass. A resistive film strip which is in electrical contact with the mass detects the maximum rebound of the mass and provides an electrical signal indicative of this maximum rebound. The distance that the mass rebounds after impacting the plunger is, in turn, a function of the concrete surface hardness and thus can be correlated to the compressive strength of the underwater concrete structure being measured.

A data acquisition and processing circuit comprising a microprocessor, signal conditioning electronics and a self-contained battery pack with a built in battery charger receives, processes and stores the electrical signals provided by the resistive strip. The data acquisition and processing circuit includes a peak detection circuit which captures the peak output signal from the resistive strip. This, in turn, indicates the maximum rebound of the hammer mass. The peak detection circuit then interrupts the microprocessor and sends a voltage/analog signal proportional to the maximum rebound of the mass to an analog to digital converter module which converts the analog signal to a digital data signal for processing by the microprocessor. The microprocessor then calculates the compressive strength of the underwater concrete structure under test.

It is therefore an object of the present invention to provide a general condition assessment of an underwater concrete structure such as a pier, retaining wall, easement or the like.

It is another object of the present invention to provide a means for quantifying the deterioration of an underwater concrete structure.

It is a yet another object of the present invention to provide a means whereby the compressive strength of an underwater concrete structure can be accurately measured.

It is a further object of the present invention to provide a means for the nondestructive testing of an underwater concrete structure.

Still further objects, advantages and novel features of the present invention will become apparent from the following detailed description of the invention when considered in conjunction with the drawings.

DETAILED DESCRIPTION OF THE PREFERRED EMBODIMENT

Figure 1:
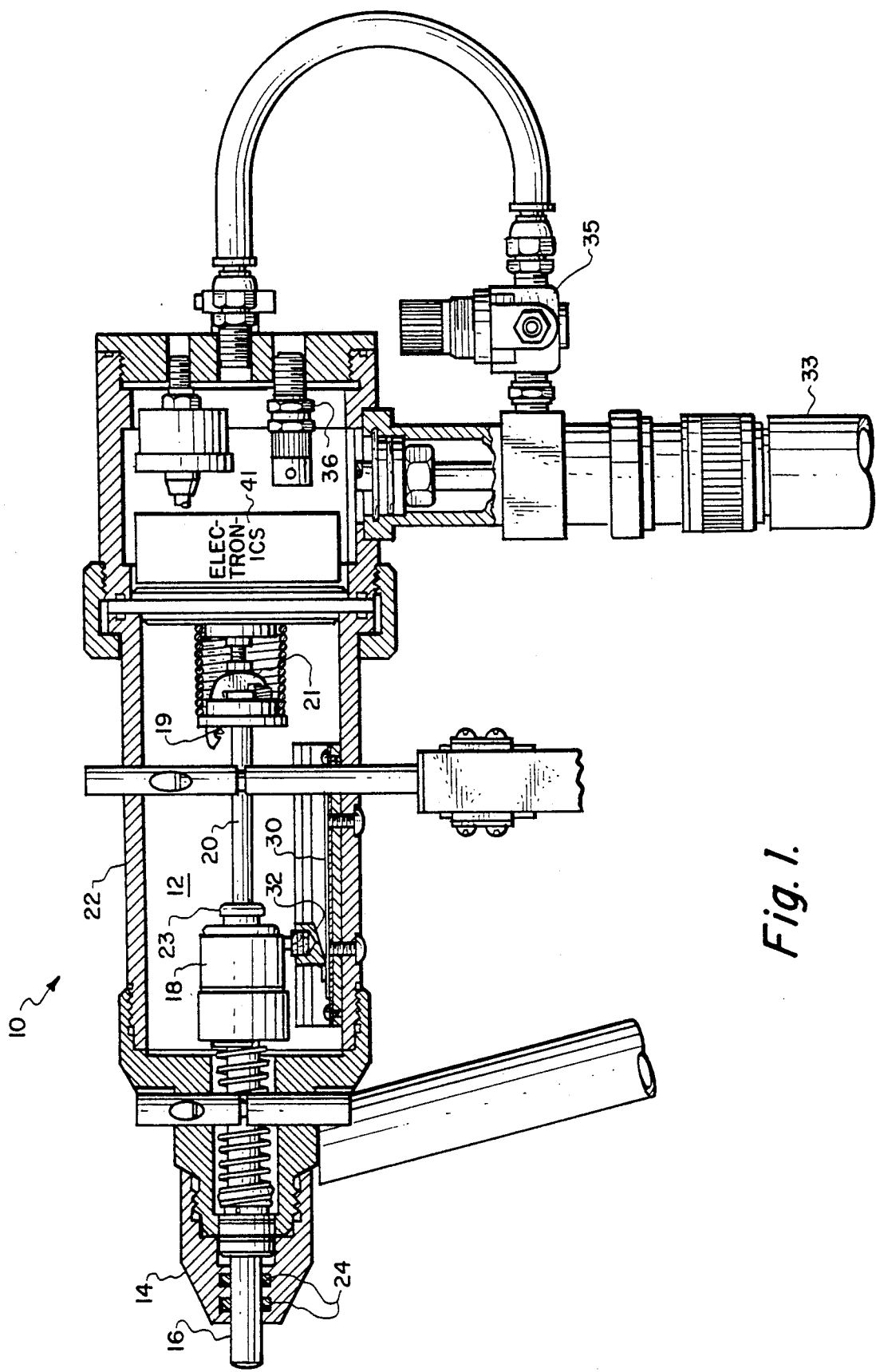
FIG. 1 is a view in section of the rebound hammer used in the present invention.

Referring to FIG. 1 there is shown a measuring apparatus, designated generally as 10, which accurately detects external and internal defects in underwater concrete structures such as piers, retaining walls, easements and the like by measuring the compressive strength of an underwater concrete structure under test. The measuring apparatus 10 comprises a rebound hammer 12 which has extending from the nose 14 thereof a plunger 16.

Rebound hammer 12 comprises a spring driven mass 18 that slides on a guide rod 20 within the rebound hammer's housing 22. To carry out a test of an underwater concrete structure plunger 16 is pressed firmly against the surface of the concrete structure under test. This releases the spring driven mass 18 from a locked position causing mass 18 to impact plunger 16 which transfers energy to the surface of the concrete structure under test. Plunger 16 reacts and re-transmits the rebound energy to mass 18 causing mass 18 to slide along guide rod 20 to the rear portion of housing 22. The harder and more compact the concrete structure the greater rebound of spring driven mass 18 with the maximum rebound height of mass 18 being indicative of the compressive strength of the concrete structure under test. The hook portion 19 of pawl 21 engages flange 23 of mass 18 holding mass 18 in the locked position until plunger 16 is pressed against the surface of the concrete structure under test.

At this time it should be noted that rebound hammer 12 is a modified commercially available Hardness Meter Model C-7311 available from James Instrument INC. of Chicago, Ill. with the modifications being as follows. To use the commercial rebound hammer under water for testing a concrete structure, rebound hammer 12 was placed inside pressure compensated aluminum housing 22 which has a double O-ring seal 24 surrounding plunger 16 at nose 14. All internal components of the commercially available rebound hammer are unchanged except for a mechanical reading pointer and the impact plunger. Plunger 16 was lengthened approximately ⅛ inch to accommodate double O-ring seal 24 with the mass and hardness of plunger 16 matching the plunger of the commercially available rebound hammer to maintain calibration. A resistive film strip 30 replaces the mechanical reading pointer to electrically detect the maximum rebound height of spring driven mass 18. In addition, an electrically conductive wiper 32 which is in slidable engagement with resistive strip 30 was attached to spring driven mass 18. Resistive strip 30, in turn, provides a minimum output voltage of 0.12 volts and a maximum output voltage of 10 volts.

Housing 22 has a depth rating of 190 feet and it is pressure compensated at 5 psi over ambient pressure. Air is supplied to rebound hammer 12 through an umbilical cable 33 via a pressure regulator 35 to maintain positive pressure differential inside housing 22. Pressure regulator 35 is adjusted to provide internal pressure within housing 22 at 4 to 6 psi. Regulator 35 then maintains pressure differential as ambient pressure changes with water depth. A relief valve 36 set at 5 psi is located at the rear end of housing 22 to prevent over pressure of the housing 22. A standard dive tank, not shown, is used for supplying air to umbilical cable 33 for pressure compensating rebound hammer 12.

Figure 2A:
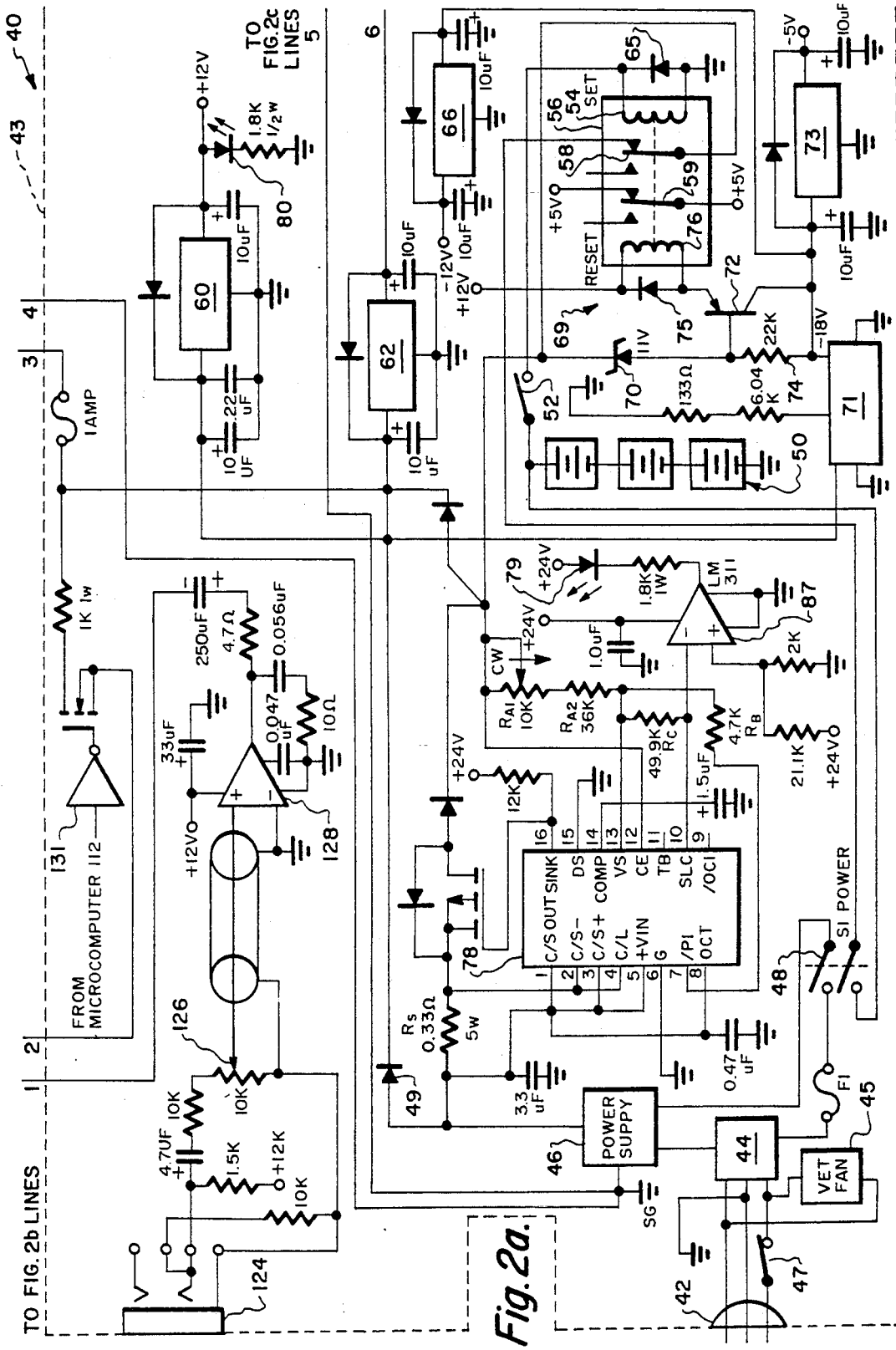
FIGS. 2a, 2b and 2c are a detailed electrical schematic of the data acquisition and processing circuit of the present invention.
Figure 2B:
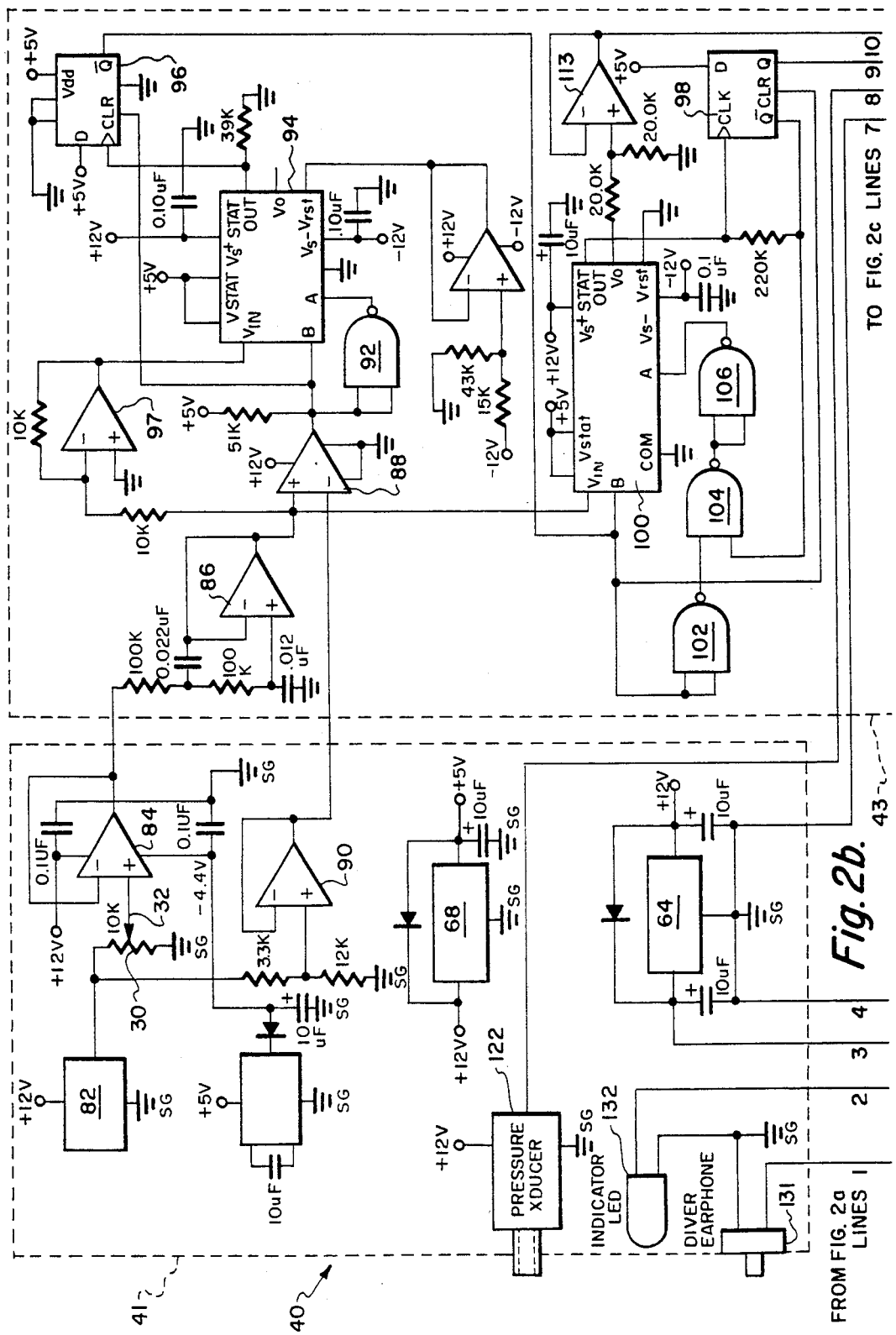
Figure 2C:
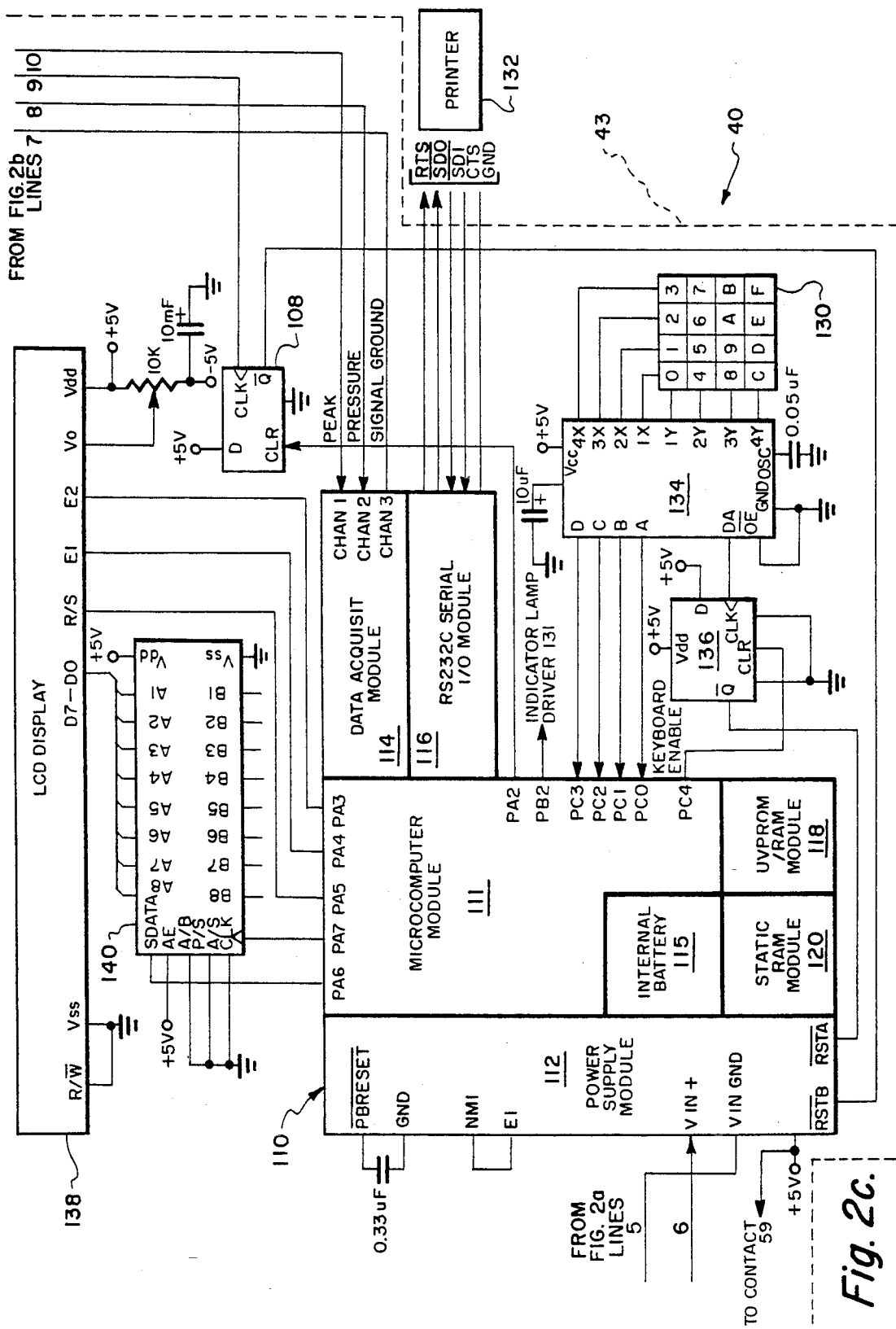

Referring to FIGS. 2a, 2b and 2c, there is shown the data acquisition and processing circuit 40 of measuring apparatus 10. The portion of the data acquisition and processing circuit 40 which is positioned within housing 22 is designated by the reference numeral 41 and the portion of data acquisition and processing circuit 40 located aboard a ship on a dock, a pier or the like is designated by the reference numeral 43. All electrical wires connecting circuit 41 to circuit 43 are positioned within umbilical cable 33, FIG. 1.

The ship board or top side portion 43 of the data acquisition and processing circuit 40 comprises a receptacle 42 which connects the data acquisition and processing circuit 40 to an external one hundred twenty volt alternating current power source. Receptacle 42 is connected to a power line filter 44 for filtering the 120 VAC which is then provided to a twenty four volt switching power supply 46 through a switch 48. Closure of switch 48 by an operator also connects a battery power supply 50 to the data acquisition and processing circuit 40. Thus, 18 to 24 VDC which is required to power portions 41 and 43 of the data acquisition and processing circuit 40 is provided by either the twenty four volt power supply 46 or battery power supply 50 which includes three six volt lead acid rechargeable batteries connected in series. Battery power supply 50 is, in turn, a self contained power source which provides for approximately eight hours of continuous power to portions 41 and 43 of the data acquisition and processing circuit 40.

At this time it should be noted that there is a vent fan 45 electrically connected via a switch 47 to recepticle 42. Vent fan 45 is used to cool a battery charger 78. Switch 47 is activated by a vent door, not shown, which is a component of the housing for the ship board or top side portion 43 of the data acquisition and processing circuit 40. When the vent door is open switch 47 is in a closed position, as shown in FIG. 2a, and vent fan 45 and power supply 44 are operational.

When portions 41 and 43 of the data acquisition and processing circuit 40 is utilizing battery 50 as the only source of power for the electrical components of the data acquisition and processing circuit 40, closure of a momentary contact switch 52 by the operator energizes a coil 54 within relay 56 which closes a contacts 58 and 59 to the set position as shown in FIG. 2a. It should be noted that prior to closing momentary contact switch 52, the operator must first close switch 48 to allow for the energization of coil 54 of relay 56.

Energizing coil 54 connects battery 50 directly to voltage regulators 60, 62, and 64 and a DC to DC converter 71 which is connected to voltage regulators 66 and 73 Voltage regulator 64 is connected directly to a voltage regulator 68. When coil 54 is energized voltage regulators 60, 62, 64, 66 and 68 and 73 respectively provide at their outputs +12 VDC, +15 VDC, +12 VDC, −12 VDC, +5 VDC and −5 VDC which is then supplied to the electrical components of portions 41 and 43 of the data acquisition and processing circuit 40.

In a similar manner, when power supply 46 is the source of power for the electrical components of circuit 40 closure of switch 48 supplies power supply 46 with 120 VAC from receptical 42. Power supply 46 then provides approximately 24 VDC and a 1.2 amp maximum current via diode 49 to voltage regulators 60, 62 64, as well as DC to DC converter 71 which provides at its output −18 VDC.

When the current drain on battery 50 results in a voltage of approximately 16.5 volts at the positive terminal of battery 50 a sensing circuit 69 comprising a twelve volt zener diode 70, transistor 72, diodes 65 and 75, and a twenty two Kohm resistor 74 activates coil 76 of relay 56 opening contacts 58 and 59 of relay 56 to a reset position which disconnects battery 50 from the electrical components of data acquisition and processing circuit 40. This sensing circuit 69 in combination with relay 56 protects battery 50 against over-discharge by isolating battery 50 from the electrical components of data acquisition and processing circuit 40. It should be noted that diodes 65 and 75 are protective diodes preventing back EMF when coils 54 and 76 are de-energized.

When battery 50 is fully charged to approximately 22 VDC, zener diode 70 maintains the base voltage of transistor 72 at a voltage level which is sufficient to restrict current flow from the emitter to the collector of transistor 72 and thereby maintain coil 76 in a nonenergized state. As battery 50 discharges the base voltage for transistor 72 decreases, the current flow through coil 76 increases and the base current for transistor 72 increases. When battery 50 discharges to approximately 16.5 VDC, the emitter to base voltage of transistor 72 will be at 0.6 VDC turning on transistor 72 allowing sufficient current flow through coil 76 to energize coil 76. The energizing of coil 76 opens contact 58 and 59 of relay 56 thereby disconnecting battery 50 from the electrical components of battery acquisition and processing circuit 40.

It should be noted that power supply module 112 of microprocessor 110 supplies a +5 VCD to contact 59 of relay 56. When coil 54 is energized contact 59 is in the position illustrated in FIG. 2a such that the +5 VDC provided by microprocessor 110 is supplied to liquid crystal display 138, Flip-Flops 96, 98, 108 and 136, sixteen key encoder 134, peak detectors 94 and 100 and the 51 Kohm resistor connected to the B input of peak detector 94. It should be noted that the transistor used is the preferred embodiment of the present invention is a Motorola Model 2N2907 PNP transistor, while the zener diode is a Motorola Model 7 1N4746 zener diode.

Figure 6:
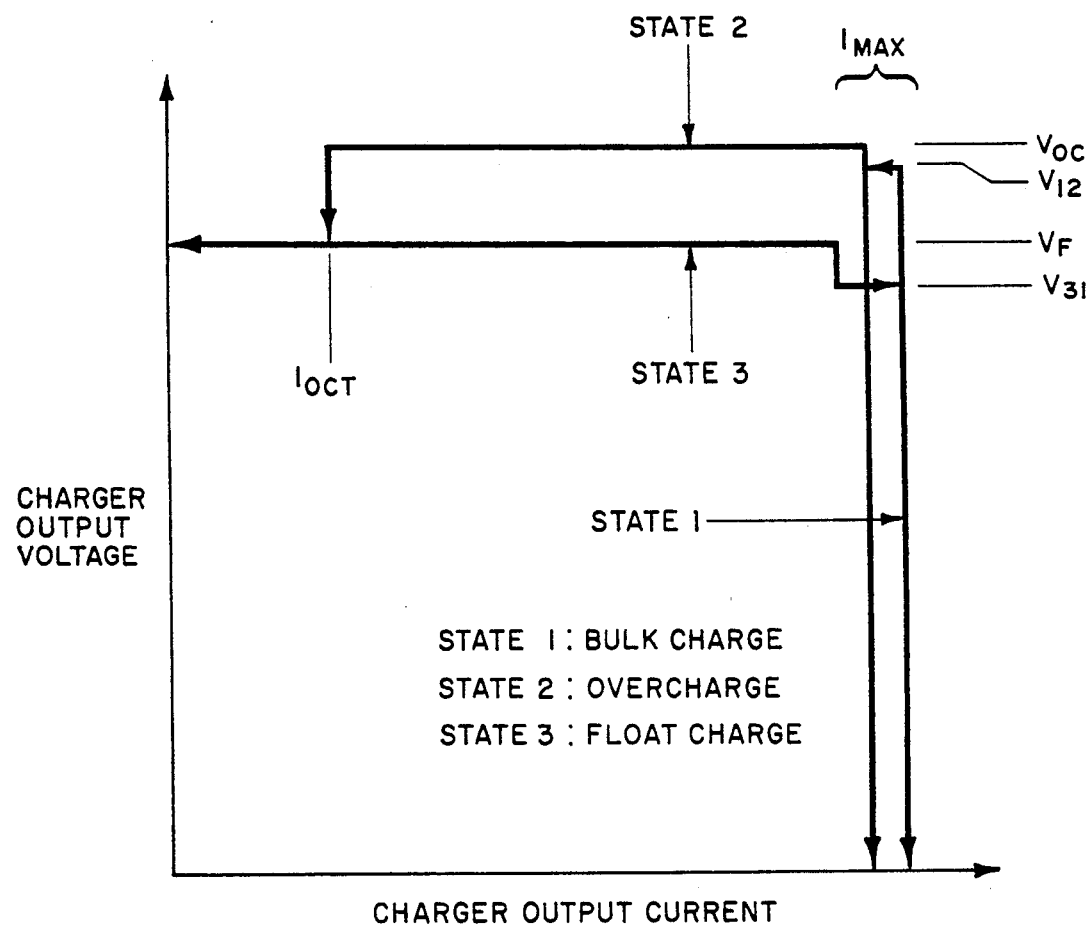
FIG. 6 is a graph illustrating the three charge states of the battery charger of the present invention.

Referring to FIGS. 2a and 6, data acquisition and processing circuit 40 also includes a battery charger 78 which is used to recharge battery 50 when power supply 46 is being utilized by circuit 40. A charge cycle begins with charger 78 in a bulk charge state (state 1) and charger 78 functioning as a constant current source that provides a constant current of $I_{MAX}$ to battery 50 which is defined by the following equation $$I_{MAX} = \frac{0.25V}{R_S} \quad (1)$$

where $R_S$ is 0.33 ohms. Either of two conditions, in turn, initiates the bulk-charge state at the beginning of the cycle. The first condition occurs when an operator connects receptacle 42 to 120 VAC and the second condition occurs while battery charger 78 is in the float state, that is battery charger 78 senses a low voltage on battery 50. This constant current bulk charge state returns seventy to ninety percent of the charge capacity of battery 50.

Charger 78 senses the battery voltage for battery 50. When the voltage reaches a transition threshold voltage $V_{12}$, charger 78 begins an overcharge cycle (state 2). $V_{12}$ is defined by the following equation $$V_{12} = 0.95 \, V_{OC} \quad (2)$$

where $V_{OC}$ is 22.2 VDC and is defined as the overcharge voltage. The overcharge voltage $V_{OC}$ may be calculated by using the following equation $$V_{OC} = V_{REF}\left(1 + \frac{R_A}{R_B} + \frac{R_A}{R_X}\right) \quad (3)$$

where $R_X$ is defined by the following equation $$R_X = \frac{R_B R_C}{R_B + R_C} \quad (4)$$

and $R_A = R_{A1} + R_{A2}$, $R_B$ is 4.7 Kohms and $R_C$ is 49.9 Kohms. $R_A$ is, in turn, determined by adjusting ten kohm variable resistor $R_{A1}$ such that the overcharge voltage is set at 22.2 VDC. The overcharge voltage is, in turn, measured at the positive terminal of battery 50.

During the overcharge state, charger 78 regulates battery 50 at $V_{OC}$ until the charge rate drops to a specified transition current $I_{OCT}$ which is defined by the following equation $$I_{OCT} = \frac{0.025V}{R_S} \quad (5)$$

where $R_S$ is 0.33 ohm.

When the current provided by battery charger 78 tapers to $I_{OCT}$ with the battery's 50 voltage at $V_{OC}$ the capacity of battery 50 is nearly one hundred percent. At this point, battery charger 78 functions as a voltage regulator with a precise output defined by the following equation $$V_F = V_{REF}\left(1 + \frac{R_A}{R_S}\right) \quad (4)$$

where $R_A = R_{A1} + R_{A2}$, $R_S$ is 33 ohm and $V_{REF}$ is a reference voltage for battery charger 78 which is temperature dependent and is typically between 2.425 VDC and 2.18 VDC for a temperature range of zero to seventy degrees celsius.

The output voltage of battery charger 78 is now in the third state $V_F$, that is the float state. If the charge current increases sufficiently to reach $I_{MAX}$ while in float state $V_F$ then $V_{31}$ is reached which leads to the state 1 bulk charge condition after $I_{MAX}$ is reached.

$V_{31}$ is, in turn defined by the following equation $$V_{31} = 0.9 \, V_F \quad (7)$$

At this time it should be noted that a complete written description of the operation of the battery charger circuit used in the present invention is provided in an article entitled "IC Provides Optimal Lead-Acid-Battery Charger Cycles" by Richard Valley published in Engineering Design News, Oct. 31, 1985, pages 161-178, which is incorporated by reference. It should also be noted that the constant current bulk charge first returns seventy to ninety percent of battery capacity and the remaining charge capacity is returned during the elevated constant voltage overcharge. In addition, it should be noted that external resistors $R_{A1}$, $R_{A2}$, $R_B$, $R_C$ and $R_S$ determine the programming of all battery charger's 78 voltage and current levels which are set forth in equations one through seven.

The float charge state is sensed by a comparator 87 which activates a light emitting diode 79 to indicate battery 50 is fully charged. The battery charger used in the preferred embodiment of the present invention is a Unitrode Model UC3906 battery charger integrated circuit.

It should also be noted that a light emitting diode 80 is connected to the output of voltage regulator 60 to indicate that either power supply 46 or battery 50 is operational and thereby supplying current to the electrical components of data acquisition and processing circuit 14.

Figure 3:
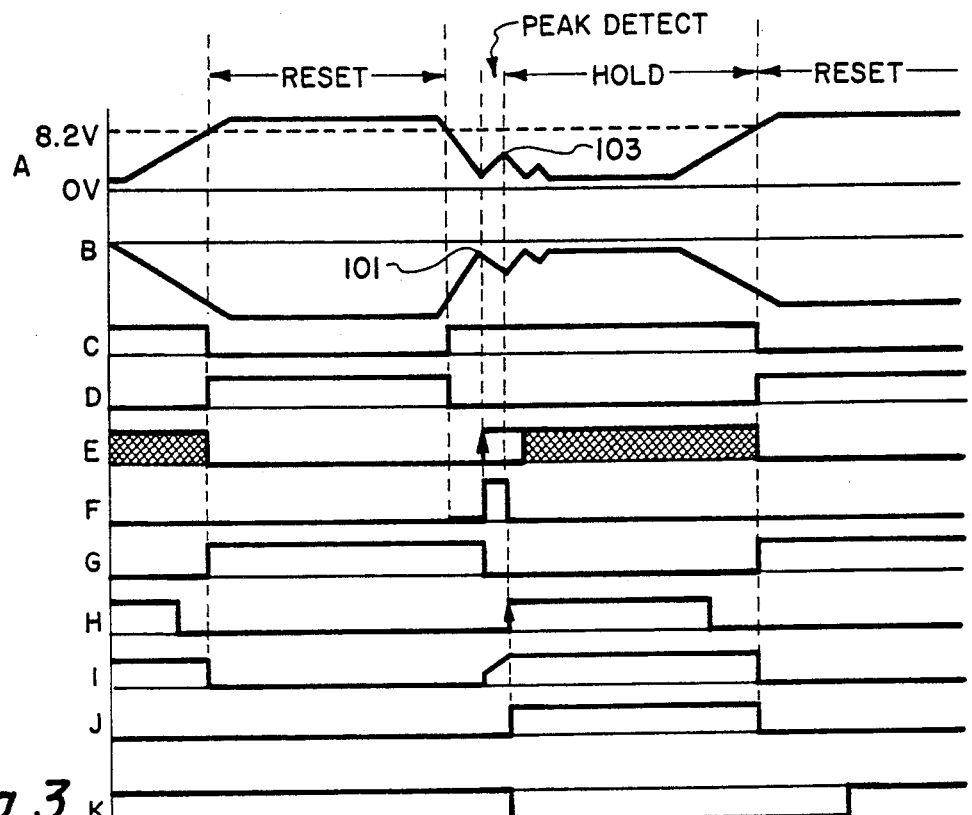
FIGS. 3A-3K are timing diagrams illustrating the waveform outputs of various electrical components of the circuit of FIG. 2.

Referring to FIGS. 1, 2a, 2b and 2c, resistive strip 30 which is a position sensing transducer for rebound mass 18 is supplied a temperature compensated stable 10 VDC by a power supply 82. By utilizing a stable temperature compensated source of power 82 apparent differences in concrete hardness measurements due to drift in the resistive strip supply voltage are minimized. When rebound mass 18 is in the cocked position, the output voltage provided by resistive strip is approximately 8.5 volts as is best illustrated by FIG. 3A. Pressing plunger 16 against an underwater concrete surface whose hardness/compressive strength is being measured will result in rebound mass 18 being released and resistive strip 30 providing the signal/waveform of FIG. 3A. The signal of FIG. 3A indicates the rebound height or distance mass 18 traverses after being released.

The signal of FIG. 3A is buffered by an operational amplifier 84 and then supplied to a low pass butterworth filter 86 which has a cutoff frequency of approximately 96 Hertz. Butterworth filter 86, in turn, eliminates jitter from the signal of FIG. 3A.

As plunger 16 is pushed further into housing 22 of rebound hammer 12, the voltage applied to the noninverting input of voltage comparator 88 increases. A point is reached just prior to the release of rebound mass 18 when the voltage applied to the noninverting input of voltage comparator 88 exceeds the approximately 8.2 volts supplied by amplifier 90 to the inverting input of voltage comparator 88. When the voltage applied to the noninverting input of voltage comparator 88 exceeds 8.2 volts the output of amplifier 88 goes to the logic one state, FIG. 3D. The logic one provided by voltage comparator 88 is supplied to a NAND gate 92 which inverts the logic one resulting in a logic zero, FIG. 3C, being provided to the A input of a peak detector 94 and a logic one, FIG. 3(D) being provided to the B input of peak detector 94 resetting peak detector 94. Resetting peak detector 94 also causes the status output of detector 94 to go to the logic zero state as shown in FIG. 3E. The logic one provided by voltage comparator 88 is supplied to the clear input of a D Flip-Flop 96 causing the not Q output of Flip-Flop 96 to go to the logic one state resetting D Flip-Flop 98.

Simultaneously, the signal of FIG. 3A is supplied to the inverting input of an amplifier 97 which inverts the signal of FIG. 3A resulting in the signal FIG. 3B being supplied to the signal input of peak detector 94.

When the signal of FIG. 3A falls below 8.2 volts the output of voltage comparator 88 goes to the logic zero state resulting in a logic zero, FIG. 3D, being provided to the B input of peak detector 94 and a logic one, FIG. 3C, being provided to the A input of peak detector 94 which enables peak detector 94. Peak detector 94 now tracks the signal of FIG. 3B until a peak value is reached. At the point in time when the signal of FIG. 3B reaches its peak value as indicated by the reference numeral 101, the status output of peak detector 94 transitions from the logic zero state to the logic one state as shown in FIG. 3E. This results in a clock pulse, FIG. 3F, being provided to the clock input of Flip-Flop 96 causing the not Q output of Flip-Flop 96 to transition from the logic one state to the logic zero state as shown in FIG. 3G.

The logic zero, FIG. 3G, at the not Q output of Flip-Flop 96 is supplied to the B input of peak detector 100, the clear input of Flip-Flop 98 and to a NAND gate 102. NAND gate 102 functions as an inverter providing a logic one to the first input of a NAND gate 104. Since the not Q output of Flip-Flop 98 is at the logic one state the output of NAND gate 104 transitions from the logic one state to the logic zero state resulting in a logic one being provided by NAND gate 106 to the A input of peak detector 100. This enables peak detector 100 allowing peak detector 100 to capture and hold the peak rebound voltage of the signal of FIG. 3A, indicated by the reference numeral 103. The peak rebound value of the signal of FIG. 3A is held by peak detector 100 until peak detector 100 is reset. It should be noted that the peak voltage 103 when held by detector 100 will decay slightly over time however this decay is minimal so as not to adversely effect the operation of data acquisition and processing circuit 40.

It should also be noted that a logic zero at both the A and B inputs of peak detector 100 creates the hold state for peak detector 100. This occurs when detector 100 detects the peak voltage value of the signal of FIG. 3A, (at point 103) causing the status output of peak detector 100 to transition from zero to one clocking Flip-Flop 98 which results in the not Q output of Flip-Flop 98 transitioning to the logic zero state. This logic zero is supplied to NAND gate 104 causing its output to transition to the logic one state. This logic one is then inverted by NAND gate 106 resulting in a logic zero at the A input of peak detector 100.

It should be noted that the peak detectors 94 and 100 used in the preferred embodiment of the present invention are Burr-Brown Model 4085 Peak Detectors.

When peak detector 100 detects the peak value 103 of the signal of FIG. 3A, a clock pulse, FIG. 3H is generated at the status output of detector 100 which is then provided to the clock input of D Flip-Flop 98. This clock pulse clocks the logic one at the D input of Flip-Flop 98 to the Q output of flip-flop 98, thereby providing a clock pulse, FIG. 3J to the clock input of D Flip-Flop 108 which causes the not Q output of Flip-Flop 108 to transition to the logic zero state thereby generating an interrupt signal, FIG. 3K, which is supplied to the /RSTB input of a microprocessor 110. The interrupt signal of FIG. 3K indicates to microprocessor 110 that a peak voltage value 103 of the signal of FIG. 3A is at the signal output $V_O$ of peak detector 100 as is best illustrated by the signal of FIG. 3(I). The peak voltage signal of FIG. 3I is supplied to an amplifier 113 which divides the signal by a factor of two to allow for processing of the signal of FIG. 3I by microprocessor 110.

The microprocessor 110 used in the preferred embodiment of the present invention is a Model 2800 Eight Bit CMOS Microcomputer System manufactured by National Semiconductor. Microprocessor 110 comprises a Model MA 2800 Microcomputer 111 and Power Supply Module 112, a Model MA 2400 Data Acquisition Module 114, a Model MA 2232 Communications Interface 116, a Model MA 2732 UVPROM/RAM Module 118 and a Model MA 2018 Static RAM Module 120.

The peak voltage 103 which is divided by two by amplifier 113 is supplied to the channel 1 input of Data Acquisition Module 114 which converts peak voltage 103 from an analog signal to digital data for processing by microprocessor 110. Channel 2 of Data Acquisition Module 114 receives an analog signal from a pressure transducer 122 which has a range of operation of 0 through 50 PSI. The analog signal provided by pressure transducer 122, in turn, indicates the pressure at the depth at which the underwater concrete structure is being tested. Channel 3 of Data Acquisition Module 114 receives signal ground.

It should be noted that signal ground originates at voltage regulator 64 and terminates at channel 3 of data acquisition module 114. Signal ground, which is illustrated as a ground with the symbol SG in FIGS. 2a, 2b and 2c, provides the ground for the electrical components of portion 41 of the data acquisition and processing circuit 40. This, in turn, allows pressure and peak value voltage measurements provided to channels 1 and 2 of data acquisition and processing module 114 to be referenced to signal ground thereby providing accurate data to microprocessor 110 for analysis by microprocessor 110.

Figure 4:
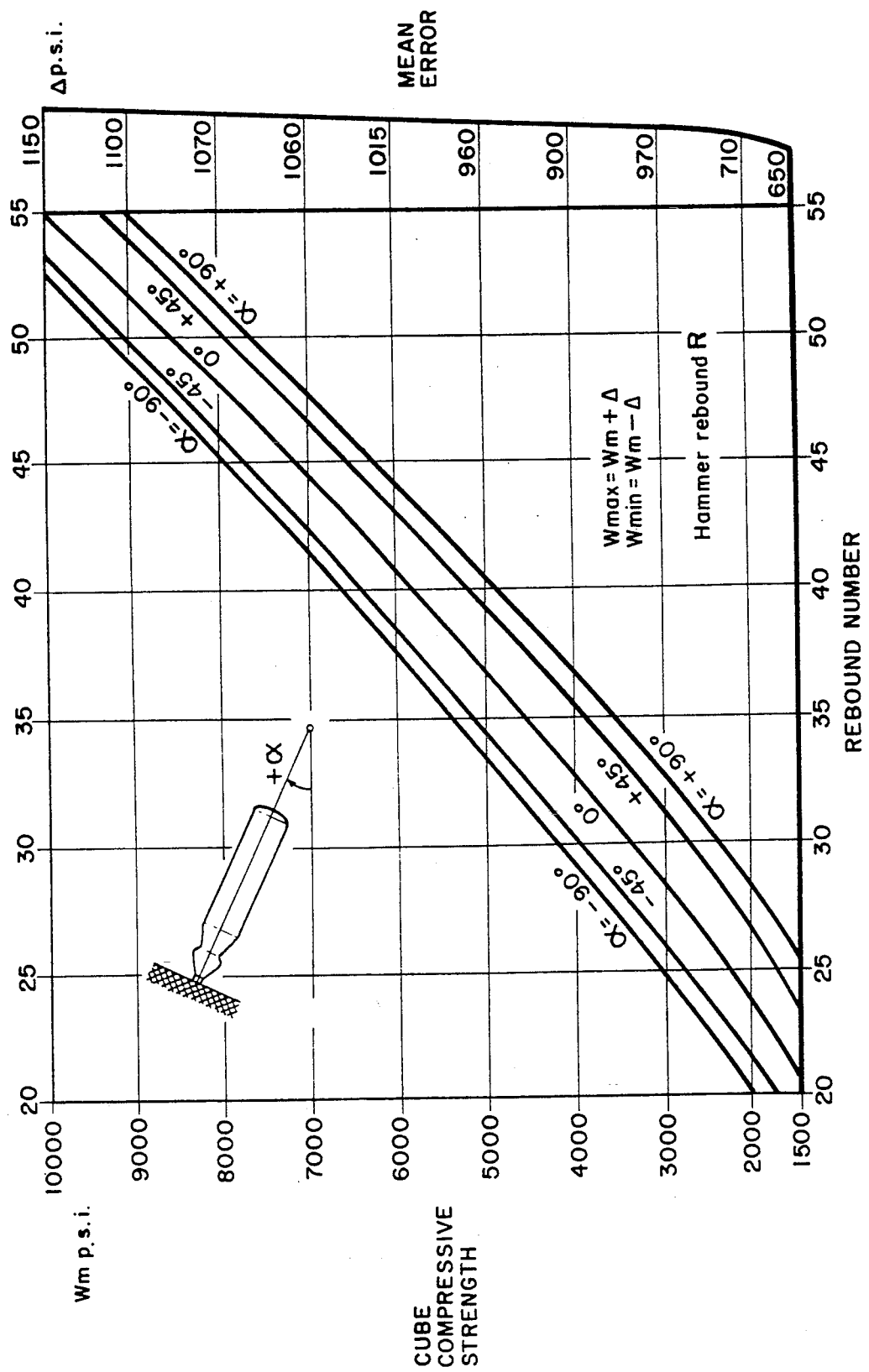
FIG. 4 is calibration chart used by the present invention to calibrate the compressive strength of the underwater concrete structure under test.

Microprocessor 110 stores all data measured during an inspection of an underwater concrete structure into static ram module 120. The program listing for the software program used to calculate the compressive strength of an underwater concrete structure being measured is stored in UVPROM/RAM Module 118 and is set forth below. The input angle alpha (see FIG. 4) of rebound hammer 12 during a measurement of an underwater concrete structure is keyed by the operator using a keypad 130. The input angle alpha of rebound hammer 12 along with the peak rebound value as represented by point 103 of the waveform of FIG. 3A is used by the microprocessor software to calculate the compressive strength of the underwater concrete structure under test in accordance with the calibration chart illustrated in FIG. 4.

A status light 132 turns on when measuring apparatus 10 is ready for collecting data and turns off when a predetermined number of measurements have been made. Generally between three and eighteen measurements are taken at each test location of the concrete underwater structure being tested with the recommended number of measurements being twelve. The multiple number of measurements allows microprocessor 110 to calculate the mean value and standard deviation of the measurements after discarding the minimum and maximum values.

After completing the inspection of the underwater concrete structure, the test results from the inspection can transferred via RS232 module 116 to a printer 132 in a report format. This report typically includes the following information which is entered by the operator using keypad 130, FIG. 5, or provided by microprocessor 110 as a result of the compressive strength measurements of the structure under test. This report includes the location of the concrete structure under test; the depth of each measurement, the number of data samples collected for each test and the estimated strength of the concrete structure under test. The estimated strength of the concrete structure under test is the estimated compressive strength of the concrete based upon the chart of FIG. 4 which relates a corrected rebound number to the comprehensive strength of a reference concrete cube consisting of a good quality aggregate and Portland cement. The corrected rebound number which is based on the value measured during a calibration check is defined by the expression:

$$R = r \times 80/n \times Ra \quad (1)$$

where R is the normalized rebound number, r is the measured rebound numbers as provided by the signal output of peak detector 100, n is the number of measurements and Ra is the calibration rebound value. Ra is determined using a calibration anvil made of hardened steel and has normal value of 80 with a standard deviation of 2 or less.

Figure 5:
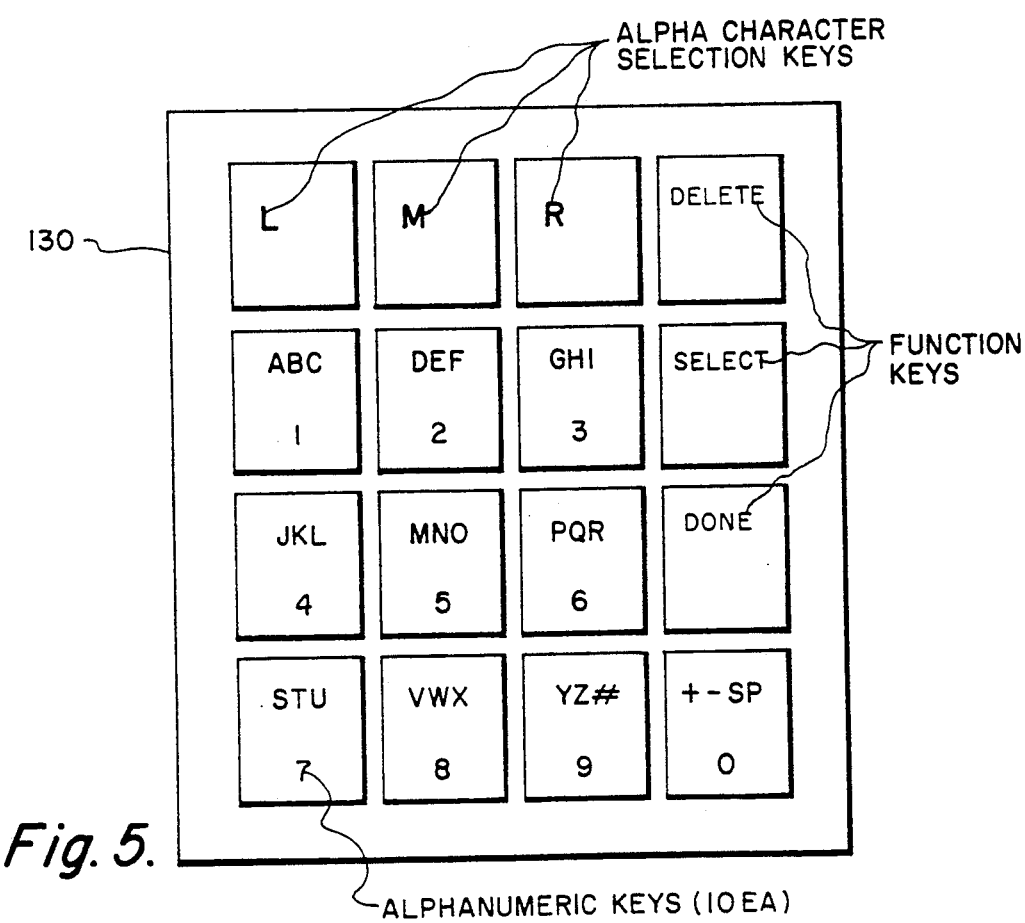
FIG. 5 illustrates the keypad for operator data entry used with the present invention.

Referring to FIGS. 2 and 5, keypad 130 is used by the operator to input certain digital data/information into microprocessor 110 such as the number of measurements to be made on a concrete structure under test. When the operator desires to enter data into microprocessor 110 a sixteen key encoder 134 which is electrically coupled to keypad 130 provides a logic zero to one transition at its DA output (data available). This logic zero to one transition clocks the logic one at the D input of Flip-Flop 136 to the Q output thereof which causes the not Q output of Flip-Flop 136 to transition from the logic one to the logic zero state thereby providing an interrupt to the /RSTA input of microprocessor 110. This interrupt provided by Flip-Flop 136 indicates to microprocessor 110 that encoder 134 is ready to provide data to microprocessor 110.

At this time it should be noted that the encoder used in the preferred embodiment of the present invention is a CMOS key encoder, Model MM74C992 16 Key Encoder manufactured by National Semiconductor.

Referring to FIG. 5 the functions of the keys on keypad 130 are briefly described as follows: L selects the alpha character located in the left hand corner of each alphanumeric key; M selects the alpha character located in the middle of each alphanumeric key and R selects the alpha character located in the right hand corner of each alphanumeric key. DELETE allows deletion of the last entry without affecting other data entered; SELECT allows a cursor to be moved around liquid crystal display 138 to select a desired function and DONE allows data to be entered into the static RAM module 120 of microprocessor 110 or executes the selected function. The alphanumeric keys "0-9, A-Z, +, −, #, SP" allow either numbers or letters to be entered microprocessor 110 via encoder 134. Numbers are selected by pressing the desired key, while letters are entered by pressing a position key (either L, M or R) and the key with the desired letter on it. A blank space is generated by selecting the SP key.

The liquid crystal display 138 used in the preferred embodiment of the present invention is a 4 line by 40 character LCD display Model LM44A4C40CBW LCD manufactured by Densitron. Data provided by microprocessor 110 for display by liquid crystal display 138 is provided to a serial to parallel data converter 140 which converts the data from an eight bit serial word to an eight bit parallel word and then supplies each eight bit parallel word to liquid crystal display 138 for display thereby.

Data acquisition and processing circuit 40 also has a diver communications circuit which includes a microphone jack 124 adapted to receive a microphone, not shown, a diver earphone volume control 126 connected to jack 124, an amplifier 128 connected to jack 124 and diver earphone 13 connected to the output of the amplifier 128. The diver communications circuit allows for ship or shore to diver communication with the diver using rebound hammer 12 to test an underwater concrete structure for deterioration.

From the foregoing it may readily be seen that the subject invention comprises a new, unique and exceedingly useful rebound hammer for measuring the hardness of a concrete structure which constitutes a considerable improvement over the known prior art. Obviously many modifications and variations of the present invention are possible in light of the above teachings. It is therefore to be understood that within the scope of the appended claims the invention may be practiced otherwise than as specifically described.

```
C*********************************************************************
C                                                                     *
C       SCHMITT HAMMER- mathemtical routines and some logic parts     *
C                                                                     *
C                                                                     *
C*********************************************************************
C
        SUBROUTINE CALCS
        INTEGER  CALMAX,VDBARR,NCAL,NCALS,NDAQ,CALCJB
        INTEGER  RCORR,RMEAN,STDDEV,STREN,CALVAL
C
        COMMON/VAR/CALMAX,VDBARR,NCAL,NCALS,NDAQ,CALCJB,IFLAG,ITILT,
     1  IDEPTH,RCORR,RMEAN,STDDEV,STREN,CALVAL(18),ADCH(8)
C
        GOTO(10,20),CALCJB
10      HAMRDG=(ADCH(1)-ADCH(3))*27.82-9
        DEPRDG=(ADCH(2)-ADCH(3))*22.5-55.5
        IDEPTH=IFIX(DEPRDG)
        IDEPTH=IABS(IDEPTH)
        IHAM=IFIX(HAMRDG)
        IHAM=IABS(IHAM)
        NCALS=NCALS+1
        CALVAL(NCALS)=IHAM
        RETURN
C
20      MAX=-1000
        MIN=1000
        IMAX=1
        IMIN=2
        DO 24 I=1,NCALS
        IF(CALVAL(I).GT.MIN)GOTO 22
        MIN=CALVAL(I)
        IMIN=I
        GOTO 24
22      IF(CALVAL(I).LT.MAX)GOTO 24
        MAX=CALVAL(I)
        IMAX=I
24      CONTINUE
C
        SUM=0.
        SQSUM=0.
        DO  26  I=1,NCALS
        IF(I.EQ.IMAX)GOTO 26
        IF(I.EQ.IMIN)GOTO 26
        RVAL=FLOAT(CALVAL(I))
        SUM=RVAL+SUM
        SQSUM=RVAL*RVAL+SQSUM
26      CONTINUE
        COUNT=FLOAT(NCALS-2)
        XMEAN=SUM/COUNT
        XDEV=SQSUM-XMEAN*SUM
        XDEV=XDEV/COUNT
        XDEV=SQRT(XDEV)
        IF(IFLAG.NE.0)GOTO 260
        RCAL=XMEAN
        GOTO 40
260     IF(RCAL.NE.0.0)XCORR=XMEAN*80./RCAL
        XSQUAR=XCORR*XCORR
        XCUBE=XSQUAR*XCORR
C
        NTILT=1
        IF(ITILT.LT.157)NTILT=2
        IF(ITILT.LT.112)NTILT=3
        IF(ITILT.LT. 67)NTILT=4
        IF(ITILT.LT. 22)NTILT=5
C
        GOTO(30,32,34,36,38),NTILT
C       +90 degrees  NTILT=1     180DEG          up
30      RSTREN=-1277.63 -15.7988*XCORR +5.60719*XSQUAR -.0349861*XCUBE
        GOTO 40
C
C       +45 degrees NTILT=2      135DEG     slant up
32      RSTREN= 319.368 -119.637*XCORR +8.42193*XSQUAR -.0598422*XCUBE
        GOTO 40
C
C       0 degrees   NTILT=3      90 DEG     horizontal
34      RSTREN=-499.582 +10.5961*XCORR +4.75302*XSQUAR -.0268230*XCUBE
        GOTO 40
C
```

```
C       -45 degrees  NTILT=4    45 DEG   slant down
36      RSTREN=-1148.65 +85.5079*XCORR +3.34875*XSQUAR -.0193773*XCUBE
        GOTO 40
C
C       -90 degrees  NTILT=5    00 DEG   down
38      RSTREN=-1124.38 +106.529*XCORR +2.71849*XSQUAR -.0133531*XCUBE
C
40
        STREN=IFIX(RSTREN)
        RCORR=IFIX(XCORR)
        RMEAN=IFIX(XMEAN)
        STDDEV=IFIX(XDEV)
        RETURN
C
        END

TITLE UTIL.MAC

;***********************************************************************
;
;
;       This module handles LCD drivers and various utilities
;       for the system.
;
;       SCHMITT HAMMER- instrument to measure concrete condition
;                       underwater.
;
;       Author: Roman VSEVOLOD Kruchowy              Date: NOV 18 1987
;
;
;.XLIST
 .LIST
  PAGE
 .SALL
;
;
;POINTERS
;
PCDDR   EQU     06H        ;PORTC DATA DIRECTION REGISTER
PCIO    EQU     02H        ;port C I/O
PCBC    EQU     0AH        ;port C clear, write only
PCBS    EQU     0EH        ;port C set,write only
;
PBDDR   EQU     05H        ;PORTB DATA DIRECTION REGISTER
PBIO    EQU     01H        ;PORTB I/O REG
PBBC    EQU     09H        ;PORTB CLEAR WRITE ONLY
PBBS    EQU     0DH        ;PORTB SET WRITE ONLY REG
;
PADDR   EQU     04H        ;PORTA DATA DIRECTION REG
PAIO    EQU     00H        ;PORTA I/O REG
PABC    EQU     08H        ;PORTA CLEAR REG
;
PABS    EQU     0CH        ;PORTA SET WRITE ONLY REG
PAMDR   EQU     07H        ;MODE DEF REG PORTA T0CMR   EQU     018H       ;TIMER 0 COMMAND REG
T0LSB   EQU     010H       ;TIMER 0 LSB
T0MSB   EQU     011H       ; "      "  MSB
T0STP   EQU     014H       ; "      "  STOP REG
T0STRT  EQU     015H       ; "      "  START REG
T1CMR   EQU     019H       ;TIMER 1 COMMAND REG
T1LSB   EQU     012H       ;TIMER 1 LSB
T1MSB   EQU     013H       ; "      "  MSB
T1STP   EQU     016H       ; "      "  STOP REG
T1STRT  EQU     017H       ; "      "  START REG
;
STACK   EQU     07FFFH     ;STACK BEGIN HERE
RAMTOP  EQU     07000H
ONE     EQU     0001H
;
T0MODE  EQU     039H       ;PRESCALE =64,SINGLE READ,MODE 1
T1MODE  EQU     0A5H       ;PRESCALE =01,SINGLE READ,MODE 6
MODU1   EQU     28         ;COUNT MODULUS FOR F1 WITH 2.0 MHZ IN
MODU2   EQU     34         ;COUNT MODULUS FOR FREQ F2 WITH 2.0 MHZ IN
SEC.2   EQU     65522      ;counts per 2 sec @ 2mhz/64
MODU0   EQU     SEC.2-1    ;TIMER 0 MODULUS(2SEC)
SEC.1   EQU     32761-5          ;SEC.2/2 -5    1 sec delay NRSTA   EQU     08         ;ICRB bit position for RSTA interrupt
NRSTB   EQU     04         ; "    "    "      "   RSTB     "
```

```
NRSTC   EQU     02      ;  "    "    "    "  RSTC    "
NINTR   EQU     01      ;  "    "    "    "  INTR    "
NALL    EQU     0FH     ;ALL interrupts enabled
;
;
 PAGE
SETA    MACRO   N
        LD A,01 SHL N           ;SETS PORT A BIT N
        OUT (PABS),A
        ENDM
;
CLRA    MACRO   N
        LD A,01 SHL N           ;CLEARS PORT A BIT N
        OUT (PABC),A
        ENDM
;
APULSE  MACRO   N               ;GENERATES A PULSE ON PORT A,BIT N
        LD A,01 SHL N           ;...1...0
        OUT (PABS),A
        OUT (PABC),A
        ENDM
;
SETB    MACRO   N
        LD A,01 SHL N           ;SETS PORT B BIT N
        OUT (PBBS),A
        ENDM
;
CLRB    MACRO   N
        LD A,01 SHL N           ;CLEARS PORT B BIT N
        OUT (PBBC),A
        ENDM
;
BPULSE  MACRO   N               ;generates pulse on port B bit N
        LD A,01 SHL N
        OUT (PBBS),A
        OUT (PBBC),A
        ENDM
;
;
CPULSE  MACRO   N               ;generates pulse on port C bit N
        LD A,01 SHL N
        OUT (PCBS),A
        OUT (PCBC),A
        ENDM
;
READA   MACRO   N               ;READ PORT A BIT N
        IN A,(PAIO)
        BIT N,A
        ENDM
;
ENAICR  MACRO   N               ;enables interupts via ICRB
        LD A,N
        OUT (0BBH),A
        ENDM
;
;.XLIST
 .LIST
  PAGE
;
        ENTRY   $EX,$ERR
;
        EXT     VDBTBL,MNUTBL,KEYTBL,KELTBL,KEMTBL,KERTBL,VDBREQ
;
        EXT     RAMDISP,DISPTR,MNUPTR,VDBPTR,KEYPTR,LINPTR,COLPTR
        EXT     VARPTR,CHRMAX,CHRCNT,CHRNUM,CHRIN,CHRFLG,MNUNUM,VDBNUM
        EXT     NCAL,NUM0,NUM1,NUMD0,NUMD1,NUMD2
        EXT     ASCLEN,ASCPTR,ASCBUF,ASCEND,M24RAM
        EXT     ADBUF,PKFLG
        EXT     PRSTBL,PR$PTR
;
        PUBLIC  LCDINI,MOVRAM,MOVDIS,MOVVDB,POSCUR,CURON,MULT,PNTVDB
        PUBLIC  LINOUT,BCD2B,MNUPNT
        PUBLIC  CHRDEL,CHROUT,MNUSET,MNUIN,INCVDB,VDBSET
        PUBLIC  ADTSK
;
        DELETE  EQU     01      ;keypad codes for special keys
        SELECT  EQU     05      ;SELECT key code
        DONE    EQU     06      ;DONE key code
;
;
;
;
```

```
;********** UART interrupt ***************************
;
        ASEG
        ORG     02CH            ;RST C interrupt
        PUBLIC  UART
UART:   JP      RSTC
;
;****************************************************************
;
;       Peak detect interrupt
;
        ORG     034H            ;RSTB interrpt
        JP      PKINT
;
;****************************************************************
;
;       Keypad interrupt processing
;
        ORG     03CH            ;RSTA
KEYINT:
        PUSH    AF              ;save regs
        PUSH    DE
        PUSH    HL
        IN      A,(PCIO)        ;get coded binary input from keypad
        AND     0FH             ;use only lower 4 bits
        LD      D,00            ;initialize MSB of reg DE
        LD      E,A             ;save binary input as index to key table
        LD      HL,(KEYPTR)     ;get currently active keypad table
        ADD     HL,DE           ;generate pointer to coded character
        LD      A,(HL)          ;get the character
;
        CP      00H             ;if character is null than unacceptable input
        JP      NZ,KEYL         ;if something else than check if 'shift' char.
        LD      HL,KEYTBL       ;else reinitialize key table pointer
        LD      (KEYPTR),HL
        JP      KEYEXT          ;and exit ;*************** POWER FAIL **************
;
        ORG     066H            ;NMI
PWRFAL: HALT
        JP      PWRFAL
;
;********************** Key Processing continued ****************
;
KEYL:   CP      04              ;check if 'shift' left character table
        JP      NZ,KEYM
        LD      HL,KELTBL       ;if sopoint to left table for char input
        LD      (KEYPTR),HL
        JP      KEYEXT KEYM:   CP      03              ;check if 'shift' middle character table
        JP      NZ,KEYR
        LD      HL,KEMTBL       ;if so them point to middle table
        LD      (KEYPTR),HL
        JP      KEYEXT KEYR:   CP      02              ;check if 'shift' right is desired
        JP      NZ,REGCHR       ;if not must be a regular character
        LD      HL,KERTBL       ;else use shift right table in pointer.
        LD      (KEYPTR),HL
        JP      KEYEXT REGCHR: LD      (CHRIN),A       ;and store in character input buffer
        LD      A,01            ;set flag character has arrived
        LD      (CHRFLG),A
        LD      HL,KEYTBL       ;reset table to un-'shifted'
        LD      (KEYPTR),HL KEYEXT: CPULSE  04H             ;pulse interrupt reset line
        POP     HL              ;restore regs used.
        POP     DE
        POP     AF
        EI                      ;enable interrupts
        RET
;
;
```

```
;********************************************************************
;
;       peak interrupt processing
;
PKINT:  PUSH    AF                  ;accumulator and flags
        LD      A,01
        LD      (PKFLG),A           ;set peak detect flag to a 1
        APULSE  02                  ;reset interrupt
        POP     AF                  ;restore regs
        EI                          ;enable interrupts again
        RET                         ;and return
;
;
;*********** UART INTERRUPT PROCESSING
;
;
;
        UBASE   EQU     0C0H
        USTAT   EQU     03H+UBASE
        NRXD    EQU     01H+UBASE
        NTXD    EQU     00H+UBASE
;
        EXT     USTORE,UOCNT,UOBPTR,UICNT
;
RSTC:   PUSH    AF                  ;save regs
        PUSH    HL
        IN      A,(USTAT)           ;status byte in accum
        LD      (USTORE),A
        BIT     0,A                 ;bit 0,set?
        JP      Z,XMITIN            ;if not must be transmit intrupt
        IN      A,(NRXD)            ;else serial data in and
        LD      (UICNT),A           ;store character to signal arrival
;
XMITIN: LD      A,(USTORE)          ;get stores status byte
        BIT     7,A                 ;check if transmit reg is empty
        JP      Z,UEXIT             ;if not than exit
        LD      A,(UOCNT)           ;else check character count
        AND     A                   ;set flags
        JP      Z,UEXIT             ;if empty than exit
        LD      HL,(UOBPTR)         ;get pointer to output buffer
        LD      A,(HL)              ;get next character
        OUT     (NTXD),A            ;send out
        BIT     7,A                 ;check if last character in string
        JP      Z,UCONT             ;if not set to a 1 skip
        XOR     A                   ;else reached last character
        LD      (UOCNT),A           ;notify by set count to a zero.
UCONT:  INC     HL                  ;increment pointer to next chracter
        LD      (UOBPTR),HL         ;and save in pointer
UEXIT:  POP     HL                  ;restore regs
        POP     AF
        EI                          ;enable intupts and return
        RET
;
;
;
;********************************************************************
;
;       Cursor turn on to the appropriate display
;
        CSEG
;
CURON:  LD      A,(LINPTR)          ;determne active line number
        PUSH    AF                  ;save current active line number
        BIT     01,A                ;if 2 or 3 then display 2 active
        JP      NZ,CURD2            ; jump to display 2 active routine.
CURD1:  LD      A,02                ;else,display 1 active and
        LD      (LINPTR),A          ;          send first command to
        LD      D,LCDONF            ;display 2 to turnoff cursor
        CALL    LCDCMD
        LD      A,01
        LD      (LINPTR),A          ;and turn on cursor in display 1
        LD      D,LCDON
        CALL    LCDCMD
        JP      CUREXT
;
CURD2:  LD      A,01                ;display 2 active.
        LD      (LINPTR),A          ;else, turn off display 1 cursor
        LD      D,LCDONF            ;via command
        CALL    LCDCMD
        LD      A,02
```

```
              LD      (LINPTR),A              ;and turn on display two cursor.
              LD      D,LCDON
              CALL    LCDCMD
;
CUREXT: POP   AF                              ;get original active line number
              LD      (LINPTR),A              ;and restore.
              RET
;
;
;
;****************************************************************
;
;       Move Menu N to RAM MAP
;
MOVRAM: LD    DE,(MNUNUM)                     ;get index to active menu
              SLA     E                       ;multiply by 2,('cause words not bytes)
              LD      HL,MNUTBL               ;go to start of table addresss
              ADD     HL,DE                   ;generate index to table LD      E,(HL)                  ;get LSB of address
              INC     HL
              LD      D,(HL)                  ;and the MSB of address to menu.
              EX      DE,HL                   ;store in HL
              LD      (MNUPTR),HL             ;      and in pointer.
              LD      DE,RAMDISP              ;load destination address
              LD      BC,160                  ;character count
              LDIR                            ;and do block transfer.
              RET
;
;
;****************************************************************
;
;       Move Menu N to Display
;
MOVDIS: LD    A,00                            ;set output to display line 0
              LD      (LINPTR),A              ;in line pointer
              LD      (COLPTR),A              ;start from column 0
              LD      A,40
              LD      (CHRNUM),A              ;and 40 characters
;
              LD      HL,RAMDISP
              LD      (DISPTR),HL
              CALL    LINOUT
;
              LD      A,01                    ;set up line number
              LD      (LINPTR),A              ;store in line pointer
              LD      HL,RAMDISP+40           ;beginning of line memory
              LD      (DISPTR),HL             ;store in pointer
              CALL    LINOUT                  ;send out the line LD      A,02                    ;set up line number
              LD      (LINPTR),A              ;store in line pointer
              LD      HL,RAMDISP+80           ;beginning of line memory
              LD      (DISPTR),HL             ;store in pointer
              CALL    LINOUT                  ;send out the line
;
              LD      A,03                    ;set up line number
              LD      (LINPTR),A              ;store in line pointer
              LD      HL,RAMDISP+120          ;beginning of line memory
              LD      (DISPTR),HL             ;store in pointer
              CALL    LINOUT                  ;send out the line
;
              RET
;
;
;****************************************************************
;
;       Outputs to LCD display as specified by line pointer(LINPTR)
;       starting in column (COLPTR) and for number of characters(CHRNUM).
;       Xfers characters to LCD from memory location given by DISPTR.
;
LINOUT:
              LD      A,(LINPTR)              ;get currently active line pointer
              AND     03H                     ;strip off type of var(numeric or alpha)
              RRCA                            ;rotate right into bit 7
              RRCA                            ;rotate right into bit 6
              OR      80H                     ;set up as DD RAM command to line0
              LD      D,A                     ;or line 1
              LD      A,(COLPTR)              ;get column number
              OR      D                       ;or the two to set DDram adress
              LD      D,A
              CALL    LCDCMD                  ;send out command
              LD      A,(CHRNUM)              ;set up character couunt
```

```
            LD      C,A
            LD      HL,(DISPTR)         ;get pointer at current character
            CALL    LCDRV               ;and send out char.
            RET
;
;
;
;*************************************************************
;
;       Move CURSOR to start of currently active variable
;       as determined by column and line pointer.
;
POSCUR:     LD      A,(LINPTR)          ;get currently active line pointer
            AND     03H                 ;strip type variable bit off
            RRCA                        ;rotate right into bit 7
            RRCA                        ;rotate right into bit 6
            OR      80H                 ;set up as DD RAM command to line0
            LD      D,A                 ;or line 1
            LD      A,(COLPTR)          ;get column number
            OR      D                   ;or the two to set DDram adress
            LD      D,A
            CALL    LCDCMD              ;send out command
            LD      C,1                 ;set up character couunt
            LD      HL,(DISPTR)         ;get pointer at current character
            CALL    LCDRV               ;and send out char.
            LD      D,LCSHFL            ;and shift cursor back to left
            CALL    LCDCMD
            RET
;
;
;*************************************************************
;
;
PNTVDB:     LD      HL,VDBNUM           ;else increment index
            INC     (HL)
            CALL    VDBSET              ;get VDB and move it into currently active block
            JP      NC,PNTVDB           ;reach end? if so get first VDB
;
            LD      A,(MNUNUM)          ;get menu index
            AND     A
            JP      NZ,VDBINP           ;are we doing menu 0,if not do regular process
            LD      A,(VDBREQ)          ;if so get former position in that menuu
            DEC     A                   ;decrement it
            LD      (VDBNUM),A          ;and put it in the variable definition index
VDBINP:     LD      HL,VDBNUM           ;    increment index
            INC     (HL)
            CALL    VDBSET              ;else get VDB
            LD      A,(LINPTR)          ;is it a input variable?
            AND     40H                 ;check bit 6,if set only valid for output
            JP      NZ,VDBINP           ;if NOT set than exit
            RET                         ;else, return.
;
;
;*************************************************************
;
;
MOVVDB:     LD      HL,VDBNUM           ;else increment index
            INC     (HL)
            CALL    VDBSET              ;move in the next VDB info
            JP      C,MOVVDB            ;if at the end of list,go back to the top
            LD      A,(LINPTR)          ;else check if a input variable or output only
            AND     40H                 ;chevk bit 6
            JP      NZ,MOVVDB           ;if set get next VDB
            RET                         ;else,return
;
;*************************************************************
;
;       Move Varaible definition block to RAM,i.e.
;       moves line,col,character count to RAM and generates pointer to
;       position in RAM display for first input.
;
VDBSET:     LD      DE,(MNUNUM)         ;point to current active menu index and
            SLA     E                   ;X2 'cause table made up of word adres
            LD      HL,VDBTBL           ;associated  variable block table
            ADD     HL,DE               ;add index to table address
            LD      E,(HL)              ;pointing to indirect addresss
            INC HL                      ;get address of beginning of VDB
            LD      D,(HL)
            EX      DE,HL               ;and puut in HL rgister
;
```

```
        LD      A,(VDBNUM)          ;find current active variable
        LD      C,A                 ;index by five to the right place
        LD      D,05
        CALL    MULT                ;by uusing multiply routine
        ADD     HL,BC               ;add to beginning of table address
;
        LD      A,(HL)              ;and get line location of variable
        AND     A                   ;set flags
        JP      NZ,GETVDB           ;    zero?
        DEC     A
        LD      (VDBNUM),A          ;if so end of variables;reset variable
        SCF                         ;set flag to indicate end of VDB
        RET                         ;and return
;
GETVDB: DEC     A                   ;make line number 0-3
        LD      (LINPTR),A          ;put it into the RAM line ptr
        AND     03H                 ;strip off junk and leave line number
        LD      C,A                 ;generate offset to RAM display
        LD      D,40                ;by multiplying by 40.
        CALL    MULT                ;result in BC
;
        INC     HL                  ;point to column position
        LD      A,(HL)              ;get value
        DEC     A                   ;make col number 0-39
        LD      (COLPTR),A          ;store in RAM column pointer
        ADD     A,C                 ;add to RAM display offset
        LD      C,A                 ;and store.

INC     HL                  ;get character count for variable
        LD      A,(HL)              ;and store in RAM character count
        LD      (CHRMAX),A
;
        INC     HL                  ;get address of variable into RAM
        LD      E,(HL)              ;store in regs DE
        INC     HL
        LD      D,(HL)
        LD      (VARPTR),DE         ;than save in active variable pointer
;
        XOR     A                   ;initialize character count
        LD      (CHRCNT),A LD      HL,RAMDISP          ;finally get beginning of RAM display
        ADD     HL,BC               ;add offset to address to generate
        LD      (DISPTR),HL         ;pointer to first variable entry.
;
        LD      A,(LINPTR)          ;get print out variable index
        RRCA                        ;move to lower 3 bits
        RRCA
        RRCA
        DEC     A                   ;generate index
        AND     07H                 ;mask out all the trash
        SLA     A                   ;*2 to make word index
        LD      D,0                 ;clear out addend
        LD      E,A
        LD      HL,PRSTBL           ;get address of printout table
        ADD     HL,DE               ;generate indirect address to print line
        LD      E,(HL)              ;get address in table
        INC     HL
        LD      D,(HL)
        LD      (PR$PTR),DE         ;and store in the print pointer
;
        LD      A,(LINPTR)          ;get linpointer byte
        AND     A                   ;set flags to check typr of variable
        JP      P,VDBALP            ;if bit 7=0 alpha variable, and exit
        LD      HL,(VARPTR)         ;else must be numeric,get address of
        LD      E,(HL)              ;get LSB to convert,
        INC     HL                  ;assuume variable INTEGER*2
        LD      D,(HL)              ;and get MSB,store in DE
        EX      DE,HL               ;than put in to HL
        CALL    B2ASC               ;    and convert to ASCII
        LD      B,00                ;initialize character count regs
        LD      A,(CHRMAX)          ;load in chracter count
        LD      C,A
        LD      HL,ASCEND           ;get right justified address,
        AND     A                   ;clear carry and point to indexed
        SBC     HL,BC               ;ASCII output buffer
        LD      DE,(DISPTR)         ;get DEstination address
        LDIR                        ;and transfer block of chracters
;
        LD      B,00                ;initialize character count regs
        LD      A,(CHRMAX)          ;load in chracter count
        LD      C,A
```

```
        LD      HL,ASCEND           ;get right justified address,
        AND     A                   ;clear carry and point to indexed
        SBC     HL,BC               ;ASCII output buffer
        LD      DE,(PR$PTR)         ;get DEstination address,to print line
        LDIR                        ;and transfer block of chracters
;
        JP      VDBEX
;
VDBALP: LD      HL,(VARPTR)         ;get address of beginning of variable
        LD      DE,(DISPTR)         ;get destination in RAM
        LD      A,(CHRMAX)          ;number of characters
        LD      C,A                 ;into count
        LD      B,00                ;zero ouut reG B
        LDIR                        ;do block transfer
;
        LD      HL,(VARPTR)         ;get address of beginning of variable
        LD      DE,(PR$PTR)         ;get destination in RAM,print line
        LD      A,(CHRMAX)          ;number of characters
        LD      C,A                 ;into count
        LD      B,00                ;zero ouut reG B
        LDIR                        ;do block transfer
;
VDBEX:  LD      A,(CHRMAX)          ;and ship out to the LCD display
        LD      (CHRNUM),A
        CALL    LINOUT              ;sends line out to LCD
;
        AND     A                   ;clear flag indiacte done
        RET                         ;and return
;****************************************************************
;
;
;       LCD initialization routine
;
        LCDFS   EQU     00111000B   ;2 lines,5x7 dots,8 bits data
        LCDMS   EQU     00000110B   ;increment DDRam address,noshift
        LCDONF  EQU     00001100B   ;LCD display on,cursor off
        LCDON   EQU     00001111B   ;LCD display on,cursor on
        LCDCLR  EQU     01          ;clear display,all spaces
        LCSHFR  EQU     014H        ;shift cursor to right
        LCSHFL  EQU     010H        ;shift cursor to left
;
LCDINI: LD      D,LCDFS             ;initialize LCD function
        CALL    LCDCMD              ;send to command output
        LD      D,LCDFS
        CALL    LCDCMD              ;repeat
        LD      D,LCDMS             ;st up toincrement address
        CALL    LCDCMD
        LD      D,LCDON             ;turn display on
        CALL    LCDCMD
        LD      D,LCDCLR            ;clear to all spaces
        CALL    LCDCMD
        RET
;
;
;****************************************************************
;
        Liquid Display Driver:
;       Used with DENSITRON dot matrix LCD modules
;       port A outputs: PA6: data
;                       PA7: clock      0>1 xition
;                       PA5: RS    0:Inst    1:Char  register
;                       PA4: enable     1>0 xition  display 1
;                       PA3: enable     1>0 xition  display 2
;       Called with character buffer pointer in HL
;          "        "         "       count in the     C  register
;
;
        LDATA   EQU     06          ;Port A bit 6,data
        LCLK    EQU     07          ;Port A bit 7,clock
        LENA1   EQU     04          ;Port A bit 4,enable pulse display 1
        LENA2   EQU     03          ;Port A bit 3,enable pulse display 2
        LRS     EQU     05          ;Port A bit 5,register select
;
        ENTRY   LCDRV
;
LCDRV:  LD      D,(HL)              ;get character
        INC     HL                  ;point to next one
        CALL    LCDOUT              ;ship it out.
        DEC     C                   ;decrement character count
        JP      NZ,LCDRV            ;all done?
        RET                         ;if yes return.
;
```

```
;                    ********************
;       This routine toggles the RS line to ouput the byte as
;       instruction to the display
;
LCDCMD: CLRA    LRS             ;set register select line low
        CALL    LCDOUT          ;and output code in reg 'D'
        SETA    LRS             ;reset RS line back to high
        RET ;                    ***************************
;
;       Tis routine serially outpuuts the data to a CD4034 serial
;       to parallel converter and into the LCD registers
;
        CLRA    LDATA           ;clear data bit
LCDOUT: LD      B,08            ;set up bit count
LLOOP1: LD      A,D             ;transfer byte to accumulator
        RLA                     ;rotate into carry
        LD      D,A             ;and store remainder of byte
        JR      NC,LCDCP        ;in zero do a clock pulse
        SETA    LDATA           ;if not set data line to 1
LCDCP:  APULSE  LCLK            ;generate clock pulse
        CLRA    LDATA           ;reset data line to low
        DEC     B               ;decrement bit count
        JR      NZ,LLOOP1       ;if not done get next bit
        LD      A,(LINPTR)
        BIT     1,A
        JP      NZ,DISP2
DISP1:  APULSE  LENA1           ;otherwise generate
        JP      LCDEXT
DISP2:  APULSE  LENA2
;
LCDEXT: RET                     ;and done...
;
;****************************************************************
;
;       Multiply two 8 bit numbers> 16 bit result
;       reg C: multiplier
;       reg D: muultiplicand
;       reg BC: Result
;
MULT:   LD      B,0             ;initiaize most significant bit
        LD      E,09            ;set up bit count
MULT0:  LD      A,C             ;rotate least significant bit of
        RRA                     ;multiplier to carry and shift
        LD      C,A             ;low order byte in the result
        DEC     E               ;decrement bit couunt
        JP      Z,MUDONE
        LD      A,B
        JP      NC,MULT1
        ADD     A,D             ;add multiplicand to high order byte
                                ;of result if bit was a one.
MULT1:  RRA                     ;carry=0 come here,shift high order
                                ;byte of result.
        LD      B,A
        JP      MULT0
MUDONE: RET
;
;****************************************************************
;
;       EXIT CODE FOR FORTRAN COMPILER
;
$EX:    HALT
;
;
;       FORTRAN FUNCTION ERROR PROCESSING
;
$ERR:   POP HL          ;STORE POINTER TO ERROR CODE IN REG HL
        LD A,(HL)       ;ERROR CODE IN ACCUM
;       LD (ERRB),A     ;store in LSB portion of error integer
        LD A,00H
;       LD (ERRB+1),A   ;make sure MSB is a zero
;       CALL ERRS       ;output error message...
;       CALL DISOUT     ;and display
        INC HL
        PUSH HL
        RET
;
;
;
```

```
;****************************************************************
;
;       Character delete routine
;
;
CHRDEL: LD      HL,CHRCNT               ;check number of characters outputted
        LD      A,00                    ;compare to none
        CP      (HL)                    ;if down to zero
        RET     Z                       ;return
;
        DEC     (HL)                    ;else decrement character count
        LD      A,(COLPTR)              ;decrement column pointer
        DEC     A
        LD      (COLPTR),A              ;and store
        LD      HL,(DISPTR)             ;get RAM display pointer
        DEC     HL                      ;derement it
        LD      (DISPTR),HL             ;and save it
        LD      A,' '                   ;put a blank in delete character
        LD      (HL),A
        CALL    POSCUR                  ;and position cursor accordingly
        RET
;
;
;****************************************************************
;
;
;
CHROUT: LD      HL,CHRCNT               ;get adress of  character counter
        LD      A,(CHRMAX)              ;put maximum in to accumulator
        CP      (HL)                    ;and do a compare
        RET     Z                       ;if maximum reached than return
;
        LD      A,(LINPTR)              ;find type of variable
        AND     A                       ;check bit 7=1,numeric
        JP      P,ALPOUT                ;if 0 than alpha
        LD      A,(CHRIN)               ;get character
        CP      '0'                     ;is it in the numeric range
        RET     C                       ;if less than zero exit
        CP      '9'+1                   ;if greater than 9
        RET     NC                      ;exit also
;
ALPOUT: INC     (HL)                    ;else,increment character count
        LD      A,(CHRIN)               ;get charcater
        LD      HL,(DISPTR)             ;get current pointer RAM display
        LD      (HL),A                  ;and load character into RAM
        LD      A,01                    ;set up a transfer of one
        LD      (CHRNUM),A              ;character to the LCD display
        CALL    LINOUT                  ;call for transfer
        LD      HL,(DISPTR)             ;get the pointer again
        INC     HL                      ;increment and
        LD      (DISPTR),HL             ;   save.
        LD      A,(COLPTR)              ;get column pointer
        INC     A                       ;increment it and
        LD      (COLPTR),A              ;save it also
        RET
;
;****************************************************************
;
;
;
MNUSET: CALL    MOVRAM                  ;move active menu to RAM
        CALL    MOVDIS                  ;copy it to the LCD display
MNUPNT: CALL    PNTVDB                  ;paint in all the variables as stored in RAM
        CALL    POSCUR                  ;move cursor to the first variable
        CALL    CURON                   ;turn on appropriate cursor
        RET
;
;****************************************************************
;
MNUIN:
        LD      A,(CHRFLG)              ;check if character came in
        AND     A                       ;set flags
        JP      Z,MNUIN                 ;if  still zero loop
        XOR     A                       ;set accumulator=0
        LD      (CHRFLG),A              ; to reset character flag.
        LD      A,(CHRIN)               ;get the character
        CP      SELECT                  ; is it a SELECT key?
        JP      Z,PROVAR                ;go process as a variable entry
        CP      DONE                    ;is it a DONE key if so process variable
        RET     NZ                      ;else retuurn
;
;                                       process variable as numeric or alpha
```

```
                                           when DONE or SELECT is keyed
PROVAR: LD      A,(CHRCNT)         ;    get character count to this point
        LD      C,A                ;store in register C
        LD      B,00               ;initialize reg B
        LD      HL,(DISPTR)        ;get pointer to current display
        SBC     HL,BC              ;generate address to beginning of variable in HL
        LD      A,(LINPTR)         ;do ASCII to binary conversion
        AND     A                  ;if bit 7=1,than an ASCII numeric variable
        JP      P,MNUALP           ;else a alpha variable
        LD      A,(CHRMAX)         ;get chrarcter length in accumulator
        CALL    ASC2B              ;do conversion
        EX      DE,HL              ;HL has binary result,store in DE for now
        LD      HL,(VARPTR)        ;find out where this variable goes
        LD      (HL),E             ;get LSB, and store
        INC     HL
        LD      (HL),D             ;get MSB, and store
        JP      MNUIEX
;
MNUALP: LD      DE,(VARPTR)        ;get destination address on RAM to move alpha
        LD      A,(CHRMAX)         ; variables, get the number of characters
        LD      C,A                ;into counter C ,HL has source address
        LD      B,0                ;initaialize B to zero
        LDIR                       ;and do block transfer
;
MNUIEX: RET
;
;
;****************************************************************************
;
;                                  output display variable for current VDB then
INCVDB: CALL    MOVVDB             ;move next variable definition block to active.
        CALL    POSCUR             ;position cursor accordingly
        CALL    CURON              ;and turn on the appropriate display cursor
        RET
;
;.XLIST
 .LIST
  PAGE
;
;
;****************************************************************************
;
;
;       MA2400 A/D converter routines using internal firmware
;       153 bytes allocated at M24RAM for its use, IX register
;       contains pointer to it.
;
        MATH    EQU     0E3EBH
        READRW  EQU     0E246H
        READRF  EQU     0E1E3H
        READO   EQU     0E180H
        AUTOGN  EQU     0E2A7H
        CHOFST  EQU     001                ;Channel offset
        GAIN1   EQU     000                ;Gain=1 code
        ADPRT0  EQU     0E0H               ;MA2400 i/o port 0;gain,channel
;
ADTSK:  LD      IX,M24RAM          ;point to allocated ram via IX
        LD      HL,M24RAM-1        ;initialize a/d conversion space
        LD      C,10               ;all ten bytes
        LD      A,00
ADLP:   INC     HL
        LD      (HL),A
        DEC     C
        JP      NZ,ADLP            ;.... done?
        LD      A,CHOFST+1         ;setup lower nibble for channel 1
        OR      GAIN1              ;upper nibble with gain=1
        LD      (M24RAM+0),A       ;load into location 0 of ram space
        CALL    ADSEQ1             ;invoke MA2400 firmware
        LD      DE,ADBUF           ;initialize byter xfer destination
        CALL    ADXFER             ;xfert real number to common ram
;
        PUSH    DE                 ;save pointer to A/D buffer
        LD      (IX+04),00         ;reset raw a/d data area
        LD      (IX+05),00
        LD      A,CHOFST+2         ;set up lower nibble for channel 2
        OR      GAIN1              ;upper for gain=1
        LD      (M24RAM+0),A       ;load into location 0
        CALL    ADSEQ2             ;invoke firmware without ref,zero check
        POP     DE                 ;get pointer to next block
        CALL    ADXFER             ;and xfer to common ram
```

```
        PUSH    DE                      ;save pointer to A/D buffer
        LD      (IX+04),00              ;reset raw a/d data area
        LD      (IX+05),00
        LD      A,CHOFST+3              ;set up lower nibble for channel 3
        OR      GAIN1                   ;upper for gain=1
        LD      (M24RAM+0),A            ;load into location 0
        CALL    ADSEQ2                  ;invoke firmware without ref,zero check
        POP     DE                      ;get pointer to next block
        CALL    ADXFER                  ;and xfer to common ram
;
        RET ;************************************************************
;
;       MA2400 firmware calls, exits with double precision
;       FPN in location 32-39 of MA24RAM block.
;
ADSEQ1: CALL    READRW                  ;reads channel and converts to fpn
        CALL    READRF                  ;reads reference
        CALL    READO                   ;reads zero
        CALL    MATH                    ;corrects,and outputs channel in volts
        RET
ADSEQ2: CALL    READRW                  ;reads channel and converts to FPN
        CALL    MATH                    ;corrects,and outputs volts fpn
        RET
;
;************************************************************
;
;       Transfers MA2400 result to common memory for FORmulaTRANslator
;       program.
;
ADXFER: LD      HL,M24RAM+36            ;point to source of fpn result
        LD      BC,04                   ;byte count for single precision
        LDIR                            ;block xfer
        RET
;
        CSEG
;
;
        PUBLIC  ASC2B,B2ASC
;
;************************************************************
;
;       on entry:
;       HL-contains beginning address of ASCII numeral (MSB)
;       A -contains the number of numerals toconvert
;
;       on exit:
;       HL-contains the binary number(16 bits)
;
;       Converts ASCII numeric string, MSB starting at HL and length in C
;       (max=6) to BCD number beginning at NUMD0 to NUMD2(3 bytes)
;       NUMD0 is the LSB of the BCD number.
;       The ASCII string is first moved to processing buffer ASCBUF
;
ASC2B:  LD      (ASCPTR),HL             ;store pointer to ASCII numeral string
        LD      (ASCLEN),A              ;as well as its lenght
;
        LD      C,06                    ;put ASCII zeroes in the processing buffer
        LD      HL,ASCBUF               ;into all 6 bytes
        LD      A,'0'
ASCLR:  LD      (HL),A                  ;do until all done
        INC     HL
        DEC     C
        JP      NZ,ASCLR
;
        LD      HL,NUMD0                ;starting at LSB byte for three bytes
        XOR     A
        LD      (HL),A                  ;do until all done
        INC     HL
        LD      (HL),A
        INC     HL
        LD      (HL),A
;
        LD      B,00                    ;time to transfer the ASCII numeric string
        LD      HL,(ASCPTR)             ;from LSB to MSB as determined by lenght
```

```
                LD      A,(ASCLEN)      ;get beginning of ASCII string add to
                LD      C,A             ;the lenght to get to the LSB address.
                ADD     HL,BC
                DEC     HL              ;adjust pointer to LSB of numeric string
                LD      DE,ASCBUF       ;get the destination address
MOVASC:         LD      A,(HL)          ;get ASCII bytes sequentially
                LD      (DE),A          ;transfer to ASCII buffer inversly LSB first
                DEC     HL              ;get next highest byte
                INC     DE              ;and increment buffer address
                DEC     C               ;uuntil all have been transferred LSB first
                JP      NZ,MOVASC       ;   to MSB last.
;
                LD      HL,ASCBUF       ;now do the ASCII to bcd conversion
                LD      DE,NUMD0        ;and put into NUMD0 as the LSB
                LD      A,(ASCLEN)      ;get the lenght of the buffer
                LD      C,A             ;save it in the counter
A2BLP:          LD      A,(HL)          ;get first ASCII numeral
                AND     0FH             ;strip off MSN 30H
                LD      B,A             ;and temporarily store
                INC     HL              ;point to next one
                LD      A,(HL)          ;get it
                AND     0FH             ;strip off ASCII stuff
                RLCA                    ;shift left 4 times to
                RLCA                    ;  upper nible.
                RLCA
                RLCA
                OR      B               ;logic or with lower nibble
                LD      (DE),A          ;and store into BCD buffer
                INC     DE              ;point to next BCD byte
                INC     HL              ;and to the next ASCII numeral
                DEC     C               ;decrement the character count by 2
                DEC     C
                JP      M,A2LPEX        ;exit for odd length ASCII numerals
                JP      NZ,A2BLP        ;exit if all characters are done.
A2LPEX:         CALL    BCD2B           ;do BCD to binary conversion
                LD      HL,(NUM0)       ;load binary result into HL
                RET
;
;
;
;***********************************************************************
;
;
;
;       BCD to Binary conversion. A 3 byte BCD number(NUMD0-NUMD2)
;       is converted to a 2 byte binary number NUM1-NUM0
;
BCD2B:          LD      HL,00           ;clear the binary number output
                LD      (NUM0),HL
                SCF                     ;set the carrry flag to indicate end processing
D2BLP:          LD      A,(NUM1)        ;get first binary number
                RR      A               ;rotate right through carry (divide by 2)
                LD      (NUM1),A        ;and save
                LD      A,(NUM0)        ;get LSB of binary number
                RR      A               ;rotate right thru carry
                LD      (NUM0),A        ;and save
                RET     C               ;if no carry not done with all 16 bits.
;
                LD      A,(NUMD2)       ;now to divide BCD number by two
                RR      A               ;rotate right thru carry
                PUSH    AF              ;save flag
                BIT     3,A             ;check to see if lower nibble >=8
                JP      Z,NXTD2H        ;if not check higher nibble
                SUB     03H             ;else subtract 3 from nibble to correct weight
NXTD2H:         BIT     7,A             ;check hihe nibble
                JP      Z,NXTD1         ;if not >= 8 than got to next number
                SUB     30H
NXTD1:          LD      (NUMD2),A
;
                POP     AF              ;get flag
                LD      A,(NUMD1)       ;now to divide BCD number by two
                RR      A               ;rotate right thru carry
                PUSH    AF
                BIT     3,A             ;check to see if lower nibble >=8
                JP      Z,NXTD1H        ;if not check higher nibble
                SUB     03H             ;else subtract 3 from nibble to correct weight
NXTD1H:         BIT     7,A             ;check hihe nibble
                JP      Z,NXTD0         ;if not >= 8 than got to next number
                SUB     30H
NXTD0:          LD      (NUMD1),A
;
                POP     AF
                LD      A,(NUMD0)       ;now to divide BCD number by two
```

```
                RR      A                       ;rotate right thru carry
                PUSH    AF
                BIT     3,A                     ;check to see if lower nibble >=8
                JP      Z,NXTDOH                ;if not check higher nibble
                SUB     03H                     ;else subtract 3 from nibble to correct weight
NXTDOH:         BIT     7,A                     ;check hihe nibble
                JP      Z,NXTD                  ;if not >= 8 than got to next number
                SUB     30H
NXTD:           LD      (NUMD0),A

POP     AF
                JP      D2BLP

;
;************    16 bit BINARY to BCD number conversion Routine (B2DEC)
;
;       NUMD0:  storage for BCD converted value
;       NUM0:   temporary storage for binary number(unsigned)
;
;       HL contains number to converted
;       ASCBUF contains the answer
; Upon completion a two byte binary number will be converted to
; a three byte binary coded decimal number unsigned. A decimal adjust
; algorithm is implemented for the conversion.
;
                NBCD    EQU     03H             ;number of decimal bytes needed
                NINDEX  EQU     NBIN*8          ;total bits necessary to shift
                NBIN    EQU     02H             ;number of binary bytes
;
B2ASC:          LD      (NUM0),HL               ;save number in NUM0
                LD      HL,NUMD0                ;point to BCD bytes
                LD      A,0
                LD      (HL),A                  ;initialize BCD to zero
                INC     HL
                LD      (HL),A
                INC     HL
                LD      (HL),A                  ;all three done
                LD      B,NINDEX                ;store number of bits to shift
AGAIN:          LD      HL,NUM0                 ;point to low byte of binary
                RL      (HL)                    ;rotate left through carry
                INC     HL                      ;point to high byte
                RL      (HL)                    ;rotate left through carry
ALGO:           LD      C,NBCD                  ;store number of BCD bytes
                LD      HL,NUMD0                ;point to beginning of BCD
DBL:            LD      A,00H                   ;clear accumlator
                ADC     A,(HL)                  ;add with carry to BCD
                DAA                             ; decimal adjust
                JP      C,ADD1                  ;number too big? goto next byte
                ADC     A,(HL)                  ;double the number
                DAA
                JR      DECN1                   ;goto next BCD byte
ADD1:           ADD     A,(HL)                  ;double the number
                DAA
                SCF                             ;set carry
DECN1:          LD      (HL),A                  ;save this byte
                INC     HL                      ;point to next BCD byte
                DEC     C                       ;number bcd bytes left
                JP      Z,DECINX                ;if zero get next binary bit
                JP      DBL                     ;otherwise do it again!
DECINX:         DEC     B                       ;reduce number of binary bit count
                JP      NZ,AGAIN                ;if not zero do it again
BCDOUT:         CALL    D2ASC                   ;call BCD to ASCII
                RET ;
;***************  BCD to ASCII Conversion Routine (D2ASC)
;
;
;       ASCINP: ASCII output buffer
;       NUMD0-NUMD2:  Contains the BCD number
;       NBCD:   Number of BCD  bytes
;
; This routine converts a stored BCD number into ASCII code and stores
;               it in ASCBUF.
;
;
                ASCNUM  EQU     30H             ;ASCII base for numbers
;
D2ASC:          LD      B,NBCD                  ;load number of decimal bytes
                LD      DE,ASCBUF-1             ;point to ASCII output buffer
                LD      HL,NUMD0+NBCD-1         ;pointer to MSB of BCD
```

```
DAGAIN: LD    A,(HL)              ;get BCD byte
        AND   OFOH                ;mask off lower nibble
        JP    NZ,FNUM             ;check if number began,i.e. not zero
        INC   DE
        LD    A,' '               ;if leading zeroes put blanks
        LD    (DE),A              ;in outpuut buffer.
;
        LD    A,(HL)              ;if zero get nuumber again
        AND   OFH                 ;now mask off upper nibble
        JP    NZ,SNUM             ;if not zero go proceess
        INC   DE                  ;else increment to next buffer location
        LD    A,' '               ;put in space if all leading zeroes
        LD    (DE),A
        DEC   HL                  ;else point to next number
        DEC   B                   ;decrement byte count
        JP    NZ,DAGAIN           ;if not do it again
;
        LD    A,'0'               ;if still zero after all that
        LD    (DE),A              ;put zero in last loacation
        JP    D2AEX               ;and exit.
;
FNUM:   LD    A,(HL)
        SRL   A                   ;shift upper nibble into lower nibble
        SRL   A
        SRL   A
        SRL   A
        OR    ASCNUM              ;add ASCII base number to upper nibble
        INC   DE
        LD (DE),A                 ;store in out buffer
;
        LD A,(HL)                 ;work on low nibble
        AND OFH                   ;strip upper nibble off
SNUM:   OR    ASCNUM              ;   add ASCII base
        INC   DE
        LD (DE),A                 ;out tobuffer
        DEC HL                    ;point to next lower BCD byte
        DEC B                     ;decrenent BCD byte count
        JP NZ,FNUM                ;do next byte if not finished
;
D2AEX:  RET
;
;
END
TITLE DAT.MAC
;
        PUBLIC  RAMDISP,DISPTR,MNUPTR,VDBPTR,KEYPTR,LINPTR,COLPTR
        PUBLIC  VARPTR,CHRMAX,CHRCNT,CHRNUM,CHRIN,CHRFLG,MNUNUM,VDBNUM
        PUBLIC  NUMO,NUM1,NUMDO,NUMD1,NUMD2
        PUBLIC  ASCLEN,ASCPTR,ASCBUF,ASCEND,M24RAM
        PUBLIC  AACT,AFAC,APRO,ADATE,APIL,STRBEG,STREND
        PUBLIC  ADAQ,ATILT
        PUBLIC  OUTPTR,OUTBUF,OUTCNT,LINCNT,PKFLG
        PUBLIC  UFLAG,UOCNT,UOBPTR,UICNT,UIBPTR,UIBUFF,USTORE,VDBREQ
        PUBLIC  PR$,PRSPTR,PRTPTR
        PUBLIC  TLTCNT,TLTACC,TLTAVG
        PUBLIC  MNUOLD
;
        DSEG
;
RAMDISP:DS    160                 ;display mapped into RAM
DISPTR: DS    02                  ;pointer to character in RAM display
MNUPTR: DS    02                  ;pointer to current menu
VDBPTR: DS    02                  ;pointer to current variable def block
KEYPTR: DS    02                  ;pointer to current keypad table
;
LINPTR: DS    01                  ;current line pointer
COLPTR: DS    01                  ;current column pointer
CHRMAX: DS    01                  ;maximum chracter count allowed current VDB
VARPTR: DS    02                  ;pointer to the numeric variable in RAM
CHRCNT: DS    01                  ;number of characters inputted
CHRNUM: DS    01                  ;number of characters to output
CHRIN:  DS    01                  ;character inputted from keypad
CHRFLG: DS    01                  ;flag 1=chararcter received 0=not rcvd
PKFLG:  DS    01                  ;flag 1=peak detection received
;
TLTACC: DS    02                  ;tilt reading accumulator
TLTCNT: DS    02                  ;tilt reading counter
TLTAVG: DS    01                  ;avg tilt reading (0-7)
;
MNUNUM: DS    02                  ;currently active index to menu table
MNUOLD: DS    02                  ;previous menu nuumber
```

```
VDBNUM:  DS     02              ;currently active index to variable def table
VDBREQ:  DS     01              ;last used VDB in menu 0
;
STRBEG:                         ;ASCII string variables
AACT:    DS     10              ;activity name
AFAC:    DS     10              ;facility name
APRO:    DS     10              ;property number
ADATE:   DS     12              ;date
APIL:    DS     01              ;pile/blhead
ADAQ:    DS     10              ;data acquisition location
ATILT:   DS     03              ;tilt status indication
STREND:
;
NUM0:    DS     01              ;temporary storage for binary number
NUM1:    DS     01              ;in ASCII/Binary conversion routine
;
NUMD0:   DS     01              ;temporary strage for BCD number in
NUMD1:   DS     01              ;ASCII/Binary conversion
NUMD2:   DS     01
;
ASCLEN:  DS     01              ;lenght of ASCII string to be converted
ASCPTR:  DS     02              ;pointer to ASCII numeric string input buffer
;
ASCBUF:  DS     06              ;temporary storage of ASCII string
ASCEND:                         ;LSB of numeric string
;
M24RAM:  DS     153
;
UFLAG:   DS     01              ;carriage return received, valid command?
USTORE:  DS     01              ;temporary storage of UART status register
UOCNT:   DS     01              ;charcter count for output
UOBPTR:  DS     02              ;pointer to UART output buffer
UICNT:   DS     01              ;input character count
UIBPTR:  DS     02              ;pointer to UART input buffer
UIBUFF:  DS     10              ;input buffer
;
PRTPTR:  DS     02              ;points to print position at output
PRSPTR:  DS     02              ;pointer to printer formatted output line
PRS:     DS     80+15           ;printer output format line
;
LINCNT:  DS     01              ;couunts lines per page
OUTCNT:  DS     01              ;counts number of block data transfers
OUTPTR:  DS     02              ;pointer to ouutput buffer(OUTBUF)
OUTBUF:  DS     160             ;description buffer storage
         DS     94*160          ;calibration and data acqisition
;
         COMMON/VAR/
         PUBLIC  NCAL,NCALS,NDAQ,CALVAL,ADBUF,CALMAX,VDBARR
         PUBLIC  CALCJB,RCORR,RMEAN,STDDEV,STREN,ITILT,IFLAG,IDEPTH
;
CALMAX:  DS     02              ;maximum number of calibration cycles
VDBARR:  DS     02              ;counter for the current VDB array element
NCAL:    DS     02              ;number of calibration cycles: INTEGER*2
NCALS:   DS     02              ;number of cal samples
NDAQ:    DS     02              ;number of data acquisition samples
CALCJB:  DS     02              ;computed GOTO variable in subroutine CALCS
IFLAG:   DS     02              ;flags claibrate(0) vs data calculations(1)
ITILT:   DS     02              ;compuuted GOTO variable for strength formula
;
IDEPTH:  DS     02              ;depth of hammer in ft
RCORR:   DS     02              ;corrected rebouund
RMEAN:   DS     02              ;mean rebound
STDDEV:  DS     02              ;std deviation
STREN:   DS     02              ;concrete strength in psi
CALVAL:  DS     18*2            ;data array to be displayed
;
ADBUF:   DS     32              ;allocate for 8 real channels
;
         END

TITLE HAM2.MAC

;
;***********************************************************************
;
;    SCHMITT HAMMER- instrument to measure concrete hardness
;                    underwter.
;
;    Author: Roman VSEVOLOD Kruchowy           Date: NOV 18 1987
;
;
```

```
        .SALL
        .XLIST
        ; LIST
        PAGE
        ;
        PCDDR   EQU     06H             ;PORTC DATA DIRECTION REGISTER
        PCIO    EQU     02H             ;port C I/O
        PCBC    EQU     0AH             ;port C clear, write only
        PCBS    EQU     0EH             ;port C set,write only
        ;
        PBDDR   EQU     05H             ;PORTB DATA DIRECTION REGISTER
        PBIO    EQU     01H             ;PORTB I/O REG
        PBBC    EQU     09H             ;PORTB CLEAR WRITE ONLY
        PBBS    EQU     0DH             ;PORTB SET WRITE ONLY REG
        ;
        PADDR   EQU     04H             ;PORTA DATA DIRECTION REG
        PAIO    EQU     00H             ;PORTA I/O REG
        PABC    EQU     08H             ;PORTA CLEAR REG
        ;
        PABS    EQU     0CH             ;PORTA SET WRITE ONLY REG
        PAMDR   EQU     07H             ;MODE DEF REG PORTA
        ;
        T0CMR   EQU     018H            ;TIMER 0 COMMAND REG
        T0LSB   EQU     010H            ;TIMER 0 LSB
        T0MSB   EQU     011H            ;  "     " MSB
        T0STP   EQU     014H            ;  "     " STOP REG
        T0STRT  EQU     015H            ;  "     " START REG
        T1CMR   EQU     019H            ;TIMER 1 COMMAND REG
        T1LSB   EQU     012H            ;TIMER 1 LSB
        T1MSB   EQU     013H            ;  "     " MSB
        T1STP   EQU     016H            ;  "     " STOP REG
        T1STRT  EQU     017H            ;  "     " START REG
        ;
        STACK   EQU     07FFFH          ;STACK BEGIN HERE
        RAMTOP  EQU     07000H
        ONE     EQU     0001H T0MODE  EQU     039H            ;PRESCALE =64,SINGLE READ,MODE 1
        T1MODE  EQU     0A5H            ;PRESCALE =01,SINGLE READ,MODE 6
        MODU1   EQU     28              ;COUNT MODULUS FOR F1 WITH 2.0 MHZ IN
        MODU2   EQU     34              ;COUNT MODULUS FOR FREQ F2 WITH 2.0 MHZ IN
        SEC.2   EQU     65522           ;counts per 2 sec @ 2mhz/64
        MODU0   EQU     SEC.2-1         ;TIMER 0 MODULUS(2SEC)
        SEC.1   EQU     32761-5         ;SEC.2/2 -5   1 sec delay IRSTA   EQU     08              ;ICRB bit position for RSTA interrupt
        IRSTB   EQU     04              ;  "    "    "       "  RSTB    "
        IRSTC   EQU     02              ;  "    "    "       "  RSTC    "
        INTR    EQU     01              ;  "    "    "       "  INTR    "
        IALL    EQU     0FH             ;ALL interrupts enabled ;
        ;
        ;
        PAGE
        SETA    MACRO   N
                LD A,01 SHL N           ;SETS PORT A BIT N
                OUT (PABS),A
                ENDM
        ;
        CLRA    MACRO   N
                LD A,01 SHL N           ;CLEARS PORT A BIT N
                OUT (PABC),A
                ENDM
        ;
        APULSE  MACRO N                 ;GENERATES A PULSE ON PORT A,BIT N
                LD A,01 SHL N           ;..1...0
                OUT (PABS),A
                OUT (PABC),A
                ENDM
        ;
        SETB    MACRO   N
                LD A,01 SHL N           ;SETS PORT B BIT N
                OUT (PBBS),A
                ENDM
        ;
        CLRB    MACRO   N
                LD A,01 SHL N           ;CLEARS PORT B BIT N
                OUT (PBBC),A
                ENDM
        ;
```

```
BPULSE   MACRO    N                ;generates pulse on port B bit N
         LD A,01 SHL N
         OUT (PBBS),A
         OUT (PBBC),A
         ENDM
;
;
CPULSE   MACRO    N                ;generates pulse on port C bit N
         LD A,01 SHL N
         OUT (PCBS),A
         OUT (PCBC),A
         ENDM
;
READA    MACRO    N                ;READ PORT A BIT N
         IN A,(PAIO)
         BIT N,A
         ENDM
;
ENAICR   MACRO    N                ;enables interupts via ICRB
         LD A,N
         OUT (0BBH),A
         ENDM
;
;.XLIST
 .LIST
  PAGE
;
;
;
;
         ENTRY    $INIT
         EXT      LCDINI,MOVRAM,MOVDIS,MOVVDB,POSCUR,CURON,PNTVDB,ASC2B,B2ASC
         EXT      CHRDEL,CHROUT,MNUSET,MNUIN,INCVDB,CALCS,ADTSK,LINOUT
         EXT      CALCS,ADTSK,VDBSET,MULT
;
         EXT      KEYTBL,KELTBL,KEMTBL,KERTBL
         EXT      RAMDISP,DISPTR,MNUPTR,VDBPTR,KEYPTR,LINPTR,COLPTR
         EXT      VARPTR,CHRMAX,CHRCNT,CHRNUM,CHRIN,CHRFLG,MNUNUM,VDBNUM
         EXT      NCALS,NCAL,NDAQ,CALVAL,NUMO,NUM1,NUMDO,NUMD1,NUMD2
         EXT      ASCLEN,ASCPTR,ASCBUF,ASCEND,M24RAM
         EXT      STRBEG,STREND,OUTPTR,OUTBUF,OUTCNT
         EXT      ADBUF
         EXT      VDBARR,CALMAX,VDBNUM,PKFLG,CALCJB,IFLAG,ITILT
         EXT      TLTTBL,ATILT,VDBREQ,USTORE
         EXT      DESCRI,PRTPTR,PR$
         EXT      MNUOLD,LINCNT
;
;*********************************************************************
;
;        Program start on power-on
;
         ASEG
         ORG 0000H
         JP       $INIT
;
;
;
;*********************************************************************
;
         ORG      100H
;
         ADPRT1   EQU      0E1H         ;MA2400 port 1,ctrl byte
;
$INIT:   LD       SP,STACK
         XOR      A                     ;reset flags and accumulator
                                        ;set mode for PORT A
         OUT      (PAMDR),A             ;   as straight I/O
;
         LD       A,010H                ;port C bit 4   set for output
         OUT      (PCDDR),A
;
         LD       A,0FCH                ;PORT A bits 2-7 set for outpuut
         OUT      (PADDR),A
;
         LD       A,04H                 ;Port B bits 2    set for output
         OUT      (PBDDR),A
;
         OUT      (T0STP),A             ;stop timer 2
         OUT      (T1STP),A             ;stop timer 1
```

```
;
        LD      A,02H                   ;enable MA2400 EPROM in E000H
        OUT     (ADPRT1),A
        LD      IX,M24RAM               ;point to MA2400 ram space
        LD      (IX+120),0E0H           ;load valuue of MA2400 base port
        LD      (IX+119),0E0H           ;MA2400 EPROM
        LD      (IX+118),000H           ;            base address
;
        LD      A,01                    ;point to display 1
        LD      (LINPTR),A
        CALL    LCDINI                  ;call LCD initialize display 1
        LD      A,02
        LD      (LINPTR),A              ;point to display 2
        CALL    LCDINI                  ;initialize display 2
;
        LD      HL,00
        LD      (MNUNUM),HL             ;point to MENU0
        LD      (MNUOLD),HL
        LD      (VDBNUM),HL             ;first variable in menu
        LD      (ITILT),HL              ;initialize tilt value bytes
;
        SETB    02                      ;turn off LED in hammer
;
;
;************ UART initialization
;
        UBASE   EQU     0C0H            ;base I/O address of UART
        BAUDN   EQU     0DH             ;baud rate code,1200
        BAUD    EQU     04H+UBASE       ;baud rate register
        USTAT   EQU     03H+UBASE       ;UART status
        SETCTL  EQU     02H+UBASE       ;control register
        NRXD    EQU     01H+UBASE       ;received data
        NTXD    EQU     00H+UBASE       ;transmit data adresss
        UCTLB   EQU     00111101B       ;intrupt mode
                                        ;NO  parity
                                        ;8 data bits,two stop
        PUBLIC  USTAT
        EXT     UIBPTR,UICNT,UOCNT,UOBPTR,UIBUFF
;
UINIT:
        LD      A,0                     ;set CTL reg TR bit =0
        OUT     (SETCTL),A              ;so that CTL can be loaded
        LD      A,UCTLB                 ;load in UART control byte
        OUT     (SETCTL),A              ;into control reg
        LD      A,BAUDN                 ;config for baud
        OUT     (BAUD),A
        LD      A,(USTAT)               ;reset any interrupts
        XOR     A                       ;initialize input charcter count
        LD      (UICNT),A
        LD      HL,UIBUFF               ;initialize  ASCII input buffer pointer
        LD      (UIBPTR),HL
        IN      A,(NRXD)                ;clear any input intrupts during boot
;
;*************************************************************
;
        LD      HL,KEYTBL               ;point to direct keypad input
        LD      (KEYPTR),HL             ; table and store in table pointer.
        XOR     A                       ;reset character received flag.
        LD      (CHRFLG),A
        LD      (PKFLG),A               ;reset peak detect flag
        LD      (VDBREQ),A              ;point to first variable in menu 0
        APULSE  02                      ;clear peak detect latch
        CPULSE  04                      ;clear keypad interrupt latch
        ENAICR  NRSTA+NRSTB+NRSTC       ;enable keypad interrupts via 74C922
                                        ; and peak detects from Burr 4085
                                        ;and the UART for commnications
        EI
;
;*************************************************************
;
;
;
        DELETE  EQU     01              ;key codes for special keys(delete)
        SELECT  EQU     05              ;select key code
        DONE    EQU     06              ;enter key code
        STNUM   EQU     07              ;startup menu position in table,first=0,..etc
        ERANUM  EQU     08              ;erase data menuu position
MAIN:
STMNU:  LD      A,STNUM                 ;get number of startup menu
        LD      (MNUNUM),A
        LD      (MNUOLD),A              ;save this menu in old menu address
        CALL    MNUSET                  ;move active menu to RAM
```

```
                                    ;copy it to the LCD display
                                    ;get variable definition block for that menu
                                    ;move cursor to the first variable
                                    ;turn on appropriate cursor
;
ST1:    CALL    MNUIN               ;get character
;
STXT1:  LD      A,(CHRIN)
        CP      DONE                ;is it a DONE key
        JP      NZ,STXT2            ;if not that than maybe SELECT key
        LD      A,(VDBNUM)          ;else get variable index number
        INC     A                   ;incement it to poin to menu table index
        CP      01                  ;was it menuu 1 request(data output)?
        JP      NZ,ST2              ;if not try next...
        XOR     A                   ;clear variable data block pointer
        LD      (VDBNUM),A          ;and store.
        LD      A,04                ;get adress of menu to outpuut data
        LD      (MNUNUM),A
        JP      DAOMNU              ;do output data routine.
;
ST2:    CP      02                  ; is it resume data acquisition)?
        JP      NZ,ST3              ;if not try next...
MNURTE: XOR     A                   ;else,
        LD      (VDBNUM),A          ;clear pointer to first variable
        LD      (MNUNUM),A
        JP      MENU0               ;and got menu 0.
;
ST3:    CP      03                  ;is it erase data?
        JP      NZ,STERR            ;if not must be error
        XOR     A
        LD      (VDBNUM),A
        LD      A,ERANUM
        LD      (MNUNUM),A
        JP      ERASMN
;
STERR:  HALT                        ;shouuld never get here.
        JP      STERR
;
STXT2:  CP      SELECT              ;is it a SELECT key
        JP      NZ,ST1              ;if not than nott accepted
        CALL    INCVDB              ;else get next VDB
        JP      ST1                 ;and wait for character
;
;************************************************************************
;
ERASMN: CALL    MNUSET              ;move active menu to RAM
;
ERAM1:  CALL    MNUIN               ;check if character came in
;
ERAXT1: LD      A,(CHRIN)           ;get the character
        CP      SELECT              ;is it the SELECT key?
        JP      NZ,ERAXT2           ;if not is an execute command(DONE)
        CALL    INCVDB              ;else go and hop to next variable
        JP      ERAM1               ;wait for key input
;
ERAXT2: CP      DONE                ;is it DONE key?
        JP      NZ,ERAM1            ;if not, then wait for another key
        LD      A,(VDBNUM)          ;else read which entry the cursor is at
        CP      00
        JP      NZ,ERAXT3           ;if not at zero,try next cursor entry
        JP      STMNU               ;else go to startup menu
;
ERAXT3: CP      01                  ;is cursor at entry 1? erase data?
        JP      NZ,ERAM1            ;must be an error go and wait for next key
        XOR     A                   ;else
        LD      (OUTCNT),A          ;initialize total line count
        LD      (LINCNT),A          ;page line count
        LD      DE,OUTBUF           ;and transfer header to top of
        LD      (OUTPTR),DE         ;   printout buffer.
        CALL    XFER
        CALL    INI                 ;initialize RAM
        JP      MNURTE              ;and return to menu zero(selection menu)
;
;
;************************************************************************
;
MENU0:  LD      A,(MNUNUM)
        LD      (MNUOLD),A
        CALL    MNUSET              ;move active menu to RAM
                                    ;copy it to the LCD display
```

```
                        ;get variable definition block for that menu
                        ;move cursor to the first variable
                        ;turn on appropriate cursor
;
MNUM1:  CALL    MNUIN           ;check if character came in
;
MNUXT1: LD      A,(CHRIN)
        CP      DONE            ;is it a DONE key
        JP      NZ,MNUXT2       ;if not that than maybe SELECT key
        LD      A,(VDBNUM)      ;else get variable index number
        LD      (VDBREQ),A      ;store it in the last request
        INC     A               ;incement it to poin to menu table index
        LD      (MNUNUM),A      ;put in menu index
        CP      01              ;was it menuu 1 request?
        JP      NZ,MNU2         ;if not try next
        XOR     A
        LD      (VDBNUM),A              ;first variable in menu
        JP      DESMNU          ;else do calibration job
;
MNU2:   CP      02              ;is it menu 2
        JP      NZ,MNU3         ;if not try next
        XOR     A
        LD      (VDBNUM),A              ;first variable in menu
        JP      CALMNU          ;else do data output job
;
MNU3:   CP      03              ;is it menu 3
        JP      NZ,MNU4         ;if not try next.
        XOR     A
        LD      (VDBNUM),A              ;first variable in menu
        JP      DAQMNU          ;else do data acqusition job
;
MNU4:   CP      04              ;is it menu 4?
        JP      NZ,MNUERR       ;if not must be error
        XOR     A
        LD      (VDBNUM),A              ;first variable in menu
        JP      DAOMNU          ;else do the preface routine
;
MNUERR: HALT                    ;shouuld never get here.
;
MNUXT2: CP      SELECT          ;is it a SELECT key
        JP      NZ,MNUM1        ;if not than nott accepted
        CALL    INCVDB          ;else get next VDB
        JP      MNUM1           ;and wait for character
;
;****************************************************************
;
;       initializes data storage and print arrays
;
XFER:   LD      HL,DESCRI       ;transfer desription menu (XFER)
XFER1:  LD      DE,(OUTPTR)     ;OR beginning of OUTBUF (XFER1)
        LD      BC,160          ;HL contains source data to
        LDIR                    ;output buffer.
;
        EX      DE,HL           ;put destination address in HL reg
        LD      A,' '+80H       ;put 2 line feedsin print ouut buffer
        LD      (HL),A          ;by puting space code with 7 bit set
        INC     HL
        LD      (HL),A
        INC     HL
;
        EX      DE,HL           ;put destination address in DE register
        LD      HL,HD1          ;initialize outpuut buffer pointer
        LD      BC,HDEND-HD1    ;get length of header
        LDIR                    ;move the block
;
        LD      C,75            ;set up counr for '*' border
        LD      A,'*'
        EX      DE,HL           ;get address of next loc into HL regs
HDRLP:  LD      (HL),A          ;ld it with a '*'
        INC     HL              ;increment to next location
        DEC     C               ;decrement count
        JP      NZ,HDRLP        ;if not done,loop again
        LD      A,'*'+80H       ;else set bit 7 to indiacte end of line
        LD      (HL),A          ;and store ythat one too.
        INC     HL              ;bump the pointer
        LD      (OUTPTR),HL     ;save last pointer to out buffer.
;
        LD      A,(OUTCNT)      ;get current line couunt total
        ADD     A,09            ;set nuumber of lines to output=9
        LD      (OUTCNT),A      ;description(4)+line(2)+header(3)=9
        LD      A,(LINCNT)      ;get current page count
        ADD     A,09            ;add header etc
```

```
            LD      (LINCNT),A              ;and save
            RET
;
INI:        LD      HL,01                   ;initialize variables,INTEGER*2
            LD      (NCAL),HL               ;calibration couuunter
            LD      HL,12                   ;number of samples
            LD      (NCALS),HL
            LD      (NDAQ),HL
            CALL    INIVAR                  ; and variable array area
;
            LD      HL,STREND               ;initialize string variable space
            LD      BC,STRBEG               ;get the beginning location and end
            XOR     A                       ;clear carry
            SBC     HL,BC                   ;get the difference
            LD      C,L                     ;store in counter
            LD      B,H
            LD      HL,STRBEG               ;get starting address
            LD      A,' '                   ;initialize to spaces
NXTSTR:     LD      (HL),A                  ;begin loading in RAM
            INC     HL
            DEC     C                       ;decrement counter
            JP      NZ,NXTSTR               ;if not done,keep at it
            RET
;
;****************************************************************
;
;
CALMNU:     CALL    INIVAR                  ;initialize array
;
            CALL    MNUSET                  ;display menuu with concomittant values
;
CALM1:      CALL    MNUIN                   ;check if character came in
;
CALXT1:     LD      A,(CHRIN)
            CP      DONE                    ;is it a 'done' key
            JP      NZ,CALXT2               ;if not try something else
MNURET:     XOR     A
            LD      (VDBNUM),A
            LD      (MNUNUM),A              ;first variable in menu
            JP      MENU0
;
CALXT2:     CP      DELETE
            JP      NZ,CALXT3
            CALL    CHRDEL                  ;do a character delete
            JP      CALM1
;
CALXT3:     CP      SELECT                  ;was it a select key
            JP      NZ,CALXT4               ;if not must be a character input
            CALL    INCVDB
            LD      A,(VDBNUM)              ;check to see if START request
            CP      04
            JP      NZ,CALM1                ;if not wait for next entry
;
            LD      HL,00                   ;start data acquisition cycle
            LD      (IFLAG),HL              ;notify FORTRAN that in calibration mode
;
            CALL    DATGET                  ;get the data
;
            LD      A,05                    ;set up for calibration result menu
            LD      (MNUNUM),A              ;set up menu number
            XOR     A                       ;point to first variable definition
            LD      (VDBNUM),A              ;  block and
            CALL    MNUSET                  ;go and display menu.
CALLP3:     CALL    KEYIN                   ;wait for key input,returns in accum
            CP      DONE                    ;looked at it long enough?
            JP      NZ,CALLP3               ;if some other character try again
            CALL    MOVOUT                  ;else save the block of data in
            LD      A,(NCAL)                ;increment calibrattion cycle counter
            INC     A
            LD      (NCAL),A                ;and save
            JP      MNURET                  ;output buffer and go to menu 0
;
CALXT4:     CALL    CHROUT                  ;output character
            JP      CALM1
;
;****************************************************************
;
;
;
DAQMNU:     CALL    MNUSET                  ;move active menu to RAM
```

```
;
DAOM1:  CALL    MNUIN           ;check if character came in
;
DAOXT1: LD      A,(CHRIN)       ;get the character
        CP      SELECT          ;is it the SELECT key?
        JP      NZ,DAOXT2       ;if not is an execute command(DONE)
        CALL    INCVDB          ;else go and hop to next variable
        JP      DAOM1           ;wait for key input
;
DAOXT2: CP      DONE            ;only DONE allowed to execute
        JP      NZ,DAOM1        ;if not wait for valid key input
        LD      A,(VDBNUM)      ;get variable index
        CP      00              ;is it zero?(i.e. PRINTER?)
        JP      NZ,DAOXT3       ;if not try,next index.
        LD      A,(OUTCNT)      ;get number of lines to output
        LD      B,A             ;store in register B
        LD      HL,OUTBUF       ;get beginning address of data lines
        LD      (PRTPTR),HL     ;and store in output pointer
BLKLP:  CALL    PRNLIN          ;print line routine
        LD      A,(CHRFLG)      ;check to see if abort is requuested?
        AND     A
        JP      NZ,DAOXT4       ;if any key pressed while in print,exit!
        DEC     B               ;decrement line counter
        JP      NZ,BLKLP        ;if not at zero than get next linek
        JP      DAOXT4          ;when all done exit.
;
DAOXT3: CP      01              ;is it a computer interface request
        JP      NZ,DAOXT4       ;if not than exit from menu
BLKRES: LD      HL,OUTBUF       ;else poin to the begining of the data
        LD      (PRTPTR),HL
        LD      A,(OUTCNT)      ;get number of lines to output
        LD      B,A             ;store in reg B
COMPIN: XOR     A               ;reset the character input byte
        LD      (UICNT),A
UINCHK: LD      A,(UICNT)       ;wait uuntil something shows up
        AND     A               ;set the flag
        JP      NZ,URCVD        ;if not zero,process command letter
        LD      A,(CHRFLG)      ;check to see if keypad inpuut occurred
        AND     A               ;set flags
        JP      NZ,DAOXT4       ;exit if any key pressed during interaction!
        JP      UINCHK          ;else keep looping wait for computer to talk
URCVD:  CP      'L'             ;is it a line outpuut command?
        JP      NZ,CMD1         ;if not is it a reset command?
        CALL    PRNLIN          ;else send out a line of output buffer space
        DEC     B               ;else decrement block count
        JP      Z,COMMSG        ;if end of blocks tell computer done
        JP      COMPIN          ;and do again
;
COMMSG: LD      HL,MSG1         ;get address of message to comp
        LD      (UOBPTR),HL     ;put in output pointer
        LD      A,01            ;reset end of line flag
        LD      (UOCNT),A
        CALL    UART            ;initiate transfer
        JP      DAOXT4          ;and exit
;
CMD1:   CP      'R'             ;is a block reset command?
        JP      NZ,COMPIN       ;if not must be error and wait for next cmd.
        JP      BLKRES          ;else point to beginning of data again.
;
DAOXT4: XOR     A               ;check key input
        LD      (CHRFLG),A      ;clear flag
        LD      A,(MNUOLD)      ;get calling menu nuumber
        CP      00
        JP      NZ,NXT1
        JP      MNURET          ;jump to menuu 0
NXT1:   CP      STNUM           ;else jump to menu startup
        JP      NZ,NXT2
        JP      STMNU
NXT2:   HALT                    ;should never get here!
        JP      NXT2
;
;****************************************************************
;
;
;
DAOMNU: CALL    INIVAR          ;initaialize variable array
;
        CALL    MNUSET          ;move active menu to RAM
;
DAQM1:  CALL    MNUIN           ;check if character came in
;
```

```
DAQXT1: LD      A,(CHRIN)
        CP      DONE            ;is it a 'done' key
        JP      NZ,DAQXT2       ;if not that than not acceptable and exit
DAQ2M0: XOR     A
        LD      (MNUNUM),A      ;point to MENU0
        LD      (VDBNUM),A      ;last referenced VDB in menu 0
        JP      MENU0
;
DAQXT2: CP      DELETE
        JP      NZ,DAQXT3
        CALL    CHRDEL          ;do a character delete
        JP      DAQM1
;
DAQXT3: CP      SELECT          ;was it a select key
        JP      NZ,DAQXT4       ;if not must be a character input
        CALL    INCVDB
        LD      A,(VDBNUM)      ;check to see if START request
        CP      04
        JP      NZ,DAQM1        ;if not wait for next entry
;
;
        LD      HL,01           ;start data acquisition cycle
        LD      (IFLAG),HL      ;notify FORTRAN that in data acqu mode
;
        CALL    DATGET          ;get the data
;
        LD      A,06            ;set up for calibration result menu
        LD      (MNUNUM),A      ;set up menu number
        XOR     A               ;point to first variable definition
        LD      (VDBNUM),A      ;   block and
        CALL    MNUSET          ;go and display menu.
DAQLP3: CALL    KEYIN           ;wait for key input,returns in accum
        CP      DONE            ;looked at it long enough?
        JP      NZ,DAQLP3       ;if some other character try again
        CALL    MOVOUT          ;else save the block of data in
        JP      DAQ2M0          ;output buffer and go to menu 0
;
DAQXT4: CALL    CHROUT          ;output character
        JP      DAQM1
;
;****************************************************************
;
;
;
DESMNU: CALL    MNUSET          ;move active menu to RAM
;
DESM1:  CALL    MNUIN           ;set flags
;
DESXT1: LD      A,(CHRIN)
        CP      DONE            ;is it a 'done' key
        JP      NZ,DESXT2       ;if not than other? Go check it
        LD      DE,OUTBUF       ;store description in description buffer
        LD      HL,RAMDISP      ;get source address
        LD      BC,160          ;number of bytes
        LDIR                    ;move the whole thing
        XOR     A
        LD      (MNUNUM),A      ;point to MENU0
        LD      (VDBNUM),A      ;first variable in menu
        JP      MENU0
;
DESXT2: CP      DELETE
        JP      NZ,DESXT3
        CALL    CHRDEL          ;do a character delete
        JP      DESM1
;
DESXT3: CP      SELECT          ;was it a select key
        JP      NZ,DESXT4       ;if not must be a character input
        CALL    INCVDB
        JP      DESM1
;
DESXT4: CALL    CHROUT          ;output character
        JP      DESM1
;
;
;****************************************************************
;
;       Outputs a line (character, bit 7 set = end of line)
;       of ASCII code through RS232 serial port
```

```
        FF      EQU     0CH
        CR      EQU     0DH
        LF      EQU     0AH
        EXT     UOCNT,UOBPTR,UART
;
PRNLIN: LD      HL,(PRTPTR)         ;get pointer to print buffer
        LD      (UOBPTR),HL         ;save in UART output buuffer pointer
        LD      A,01                ;load in character flag signal end of
        LD      (UOCNT),A           ;line in interrupt routine
        CALL    UART                ;initiate transfer via interruupts
;
PRCRLF: CALL    UWAIT               ;wait till empty
        LD      HL,(UOBPTR)         ;get current pointer in output buffer
        LD      (PRTPTR),HL         ;save cuurrent position
        LD      HL,CRLF             ;get ready to send carriage and line
        LD      (UOBPTR),HL         ;put address in UART output buffer
        LD      A,01                ;reset end of line flag
        LD      (UOCNT),A
        CALL    UART                ;begin transfer
        CALL    UWAIT               ;wait till done and return
        RET
;
;
UWAIT:  LD      A,(UOCNT)
        AND     A
        JP      NZ,UWAIT
USTLP:  IN      A,(USTAT)
        BIT     7,A
        JP      Z,USTLP
        RET
;
;
;
;
;*********************************************************************
;
;       moves copy of print line PR$ to output buffer
;
        LINMAX  EQU     58
        OUTMAX  EQU     190
;
MOVOUT: LD      A,(LINCNT)          ;get line couunt for this page
        INC     A                   ;increment it
        LD      (LINCNT),A          ;and store
        CP      LINMAX              ;compare to max for the page
        CALL    Z,NEWPAG            ;if met than generate form feed,etc
;
        LD      A,(OUTCNT)          ;get number of blocks transferred
        CP      OUTMAX              ;compare to maximum
        JP      NZ,MOV1             ;if not there yet do transfer
        LD      A,01                ;else put error code in
        PUSH    AF                  ;stack it
        JP      ERPROC              ;and proces error
;
MOV1:   INC     A
        LD      (OUTCNT),A
        LD      DE,(OUTPTR)         ;get current pointer to output buffer
        LD      HL,PR$              ;get beginning of RAM display
        LD      BC,80               ;byte couunt
        LDIR                        ;copy th entire immage to ouutput
        LD      (OUTPTR),DE         ;and store new pointer
MOVOEX: RET
;
;
;*********************************************************************
;
NEWPAG: XOR     A                   ;reset lincouunt
        LD      (LINCNT),A
        LD      DE,(OUTPTR)         ;get current pointer to outbuffer
        LD      HL,FF$              ;get pointer to form feed
        LD      BC,02               ;and character count
        LDIR                        ;xfer to output buuffer
        LD      (OUTPTR),DE         ;save pointer
        LD      A,(OUTCNT)          ;increment total line count
        INC     A
        LD      (OUTCNT),A          ;and save.
        LD      HL,OUTBUF           ;get description header saved in
                                    ;beginning of output buffer
        CALL    XFER1               ;and xfer it to the output buffer.
```

```
                RET                             ; then return

;
;
;
;********************************************************************
;
;
KEYIN:
        LD      A,(CHRFLG)              ;wait for response
        AND     A                       ;set flags
        JP      Z,KEYIN                 ;if no response keep looping
        XOR     A                       ;else reset flag
        LD      (CHRFLG),A
        LD      A,(CHRIN)               ;and pt it in the accumulator
        RET
;
;
;********************************************************************
;
;       moves a line message to display but not to RAM
;       (HL)contains address of message,(A)accumulator contains line.
;
MOVMSG:
        LD      (LINPTR),A              ;point to line 0
        XOR     A
        LD      (COLPTR),A              ;column 0
        LD      A,40
        LD      (CHRNUM),A              ;do 40 characters
        LD      (DISPTR),HL             ;put in display pointer
        CALL    LINOUT                  ;output that message to LCD
        RET
;
;
;********************************************************************
;
;               initialize variable area
;
INIVAR: LD      HL,CALVAL               ;variable array area.
        LD      C,18*2
        XOR     A
VAR0:   LD      (HL),A                  ;fill variable array area with zero
        INC     HL
        DEC     C
        JP      NZ,VAR0
        RET
;
;
;********************************************************************
;
;       fill array with readings used in calibration and data acqusition
;
DATGET: LD      A,(NCALS)               ;get number of samples to get
        CP      03                      ;is it less than 3
        JP      C,ABORET                ;if so exit
        CP      18                      ;is it greater than 18
        JP      NC,ABORET               ;also exit
        LD      (CALMAX),A              ;else, store number of samples temporary
;
        LD      HL,04                   ;point to the beginning of VALUE
        LD      (VDBARR),HL             ; display
;
        XOR     A
        LD      (PKFLG),A               ;reset the peak detect flag interrupt
        LD      (CHRFLG),A              ;reset the keypad interrupt flag
        LD      (NCALS),A               ;and start the sample count at 0
;
DATSTR: LD      A,02                    ;display the number of samples
        LD      (VDBNUM),A              ; (NCALS) currently done.
        CALL    VDBSET                  ;
;
        APULSE  02H                     ;reset the peak detect latch
        CLRB    02                      ;light the LED on hammer
;
DATLP1: LD      A,(CHRFLG)              ;read keypad flag
        AND     A                       ;any keypad action during calibration
        JP      NZ,KEYCHK               ;if so check the request made
;
```

```
            LD      A,(PKFLG)          ;is there a peak detection?
            AND     A
            JP      NZ,PKIN            ;if yes, do reading processing
;
            LD      A,04               ;put cursor on the START display
            LD      (VDBNUM),A
            CALL    VDBSET
            JP      DATLP1             ;and do again until peak detected
;
PKIN:       XOR     A                  ;peak detected,reset flag
            LD      (PKFLG),A
            SETB    02                 ;turn off LED on hammer
;
            CALL    ADTSK              ;else, get A/D readings on both channels
;
            LD      HL,01              ;set calcualation suubroutine job
            LD      (CALCJB),HL        ;at level 1
            CALL    CALCS              ;do calculations
;
            LD      A,(VDBARR)         ;else call for the display pointer
            INC     A                  ;increment by one
            LD      (VDBARR),A         ;save it and
            LD      (VDBNUM),A         ;put it in the active display block
            CALL    VDBSET             ; to display the reading
;
            LD      A,01               ;display depth
            LD      (VDBNUM),A
            CALL    VDBSET
;
            LD      HL,NCALS           ;get sample count
            LD      A,(CALMAX)         ;get maximum
            CP      (HL)               ;and do a compare
            JP      NZ,DATSTR          ;if maximum not reached than again
;
DATDON:     LD      HL,ARMSG0          ;else do done processing
            XOR     A                  ;point to line 0 of message
            CALL    MOVMSG             ;move out accept/reject message to LCD
EXTST:      LD      HL,ARMSG1          ;point to line 1 of message
            LD      A,01
            CALL    MOVMSG             ;move it to the LCD display.
DATLP2:     CALL    KEYIN              ;wait for response
            CP      SELECT             ;if SELECT than accept data as is
            JP      NZ,DATLP2          ;else some other input and ask again
;                                      ;accept data processing
            LD      HL,02              ;set CALCS subrouutine to level 2
            LD      (CALCJB),HL
            CALL    CALCS              ;call calculation subroutine
;
            LD      C,79               ;set up character count
            LD      A,' '              ;initialize to blanks,
            LD      HL,PR$             ;get starting point in format print line
PR$LP:      LD      (HL),A             ;transfer blank to formatted print line
            INC     HL                 ;increment to next address
            DEC     C                  ;decrement count
            JP      NZ,PR$LP           ;if not done,keep on truckin'
            LD      A,' '+80H          ;else,set up line terminator character
            LD      (HL),A             ;and save in print format line.
            RET
;
KEYCHK:     XOR     A                  ;check keypad input during data acq
            LD      (CHRFLG),A
            LD      A,(CHRIN)          ;check if DONE key
            CP      DONE
            JP      Z,ABORET           ;if DONE to premature exit
            JP      DATLP1             ;else no ABORT and return
ABORET:     POP     HL                 ;restore stack from CALL
            SETB    02                 ;turn off LED in hammer
            JP      MNURET             ;go to menu 0
;
;
;****************************************************************
;
;
;
ERPROC:     POP     AF                 ;pop  error code
            LD      HL,ERR01           ;memory full message output
            XOR     A                  ;set line number to 0
            CALL    MOVMSG             ;send message
            LD      HL,ARMSG1          ;send  push DONE message
            LD      A,01               ;into line 1
            CALL    MOVMSG             ;and send ouut
```

```
ERLP0:  CALL    KEYIN           ;wait for DONE key
        CP      DONE
        JP      NZ,ERLP0        ;if not keep looping
        JP      ABORET          ;else do abort to menu 0
;
;                   0         1         2         3         4
;                   1234567890123456789012345678901234567890
ARMSG0: DC      '     Push SELECT to process data       '
ARMSG1: DC      '     ============================      '
ERR01:  DC      ' Memory full-no more data logging      '
MSG1:   DC      "That's all FOLKS!"
CRLF:   DB      CR,LF+80H
FF$:    DB      CR,FF+80H
;
;**************************************************************
;
;       Header for printer output
;
;       0         1         2         3         4         5         6         7
;       12345678901234567890123456789012345678901234567890123456789012345678901234567890
HD1:DC' LOCATION   DEPTH    REBOUND   STD    REBOUND    STRENGTH   SAMPLES'
HD2:DC' (CAL NO)    (ft)    (mean)    DEV    CORRECTED    (psi)      (N)  '
HDEND:
;
END

TITLE MENU.MAC

;
;
;       ROM based Menu Forms
;
        PUBLIC  MNUTBL,VDBTBL,KEYTBL,KELTBL,KEMTBL,KERTBL,TLTTBL
        PUBLIC  PR$TBL,DESCRI
;
        EXT     NCAL,NCALS,NDAQ,CALVAL
        EXT     RCORR,RMEAN,STDDEV,STREN,IDEPTH,ITILT
        EXT     AACT,AFAC,APRO,ADATE,APIL
        EXT     ADAQ,ATILT,PR$
;
        CSEG
;
;**************************************************************
;
;       Menu Table
;
MNUTBL: DW      MENU0           ;table of default menu adresses
        DW      DESCRI
        DW      CALIB
        DW      DATACQ
        DW      DATOUT
        DW      CALRES
        DW      DATRES
        DW      STMENU
        DW      ERASMN
;
;**************************************************************
;
;       Variable Definition Block Table
;
VDBTBL: DW      MNU0DB
        DW      DESCDB
        DW      CALIDB
        DW      DAQUDB
        DW      DATODB
        DW      CRESDB
        DW      DRESDB
        DW      STMNDB
        DW      ERASDB          ;**********************************
;
;**************************************************************
;
;       Printout table for variables 0-7
;
PRSTBL: DW      PR$             ;start of variable 1
        DW      PR$+23          ;variable 2
        DW      PR$+33
        DW      PR$+41
        DW      PR$+53
```

```
        DW      PRS+13
        DW      PRS+66          ;variable 7
        DW      PRS+80          ;spill over area, all 0 variables go here
;
;
;
;**************************************************************
;
;       Menu Definitions
;
;                       0         1         2         3         4
;               1234567890123456789012345678901234567890
STMENU: DC      ' Use SELECT key for desired mode       '
        DC      '     then press DONE:                  '
        DC      ' Output Data         Erase data        '
        DC      ' Resume Data Taking                    '
;
;
;                       0         1         2         3         4
;               1234567890123456789012345678901234567890
MENU0:  DC      ' Use SELECT key for desired mode       '
        DC      '     then press DONE:                  '
        DC      ' Test Description    Calibration       '
        DC      ' Data Acquisition    Data Output       '
;
;                       0         1         2         3         4
;               1234567890123456789012345678901234567890
DESCRI: DC      'Activity:               REBOUND HAMMER '
        DC      'Facility Name:                         '
        DC      'Property Record number:                '
        DC      'Date:                                  '
;
;                       0         1         2         3         4
;               1234567890123456789012345678901234567890
CALIB:  DC      'Cal number:         Depth:      ft     '
        DC      'Samples:    Tilt:       deg  Start:    '
        DC      'Values:                                '
        DC      '                                       '
;
;                       0         1         2         3         4
;               1234567890123456789012345678901234567890
DATACQ: DC      'Data Location:      Depth:      ft     '
        DC      'Samples:    Tilt:       deg  Start:    '
        DC      'Values:                                '
        DC      '                                       '
;
;                       0         1         2         3         4
;               1234567890123456789012345678901234567890
DATOUT: DC      ' Use SELECT for desired output         '
        DC      '     then press DONE:                  '
        DC      ' PRINTER         COMPUTER        EXIT  '
        DC      '    Baud:1200  Bits:8   Parity:none    '
;
;                       0         1         2         3         4
;               1234567890123456789012345678901234567890
CALRES: DC      ' Calibration number:                   '
        DC      '             R mean:                   '
        DC      ' Standard deviation:                   '
        DC      '            Samples:                   '
;
;                       0         1         2         3         4
;               1234567890123456789012345678901234567890
DATRES: DC      'Data location:          Depth:         '
        DC      '        R mean:         R corr:        '
        DC      'Standard deviation:     Samples:       '
        DC      ' Concrete Strength:     PSI            '
;
;                       0         1         2         3         4
;               1234567890123456789012345678901234567890
ERASMN: DC      ' Use SELECT key for desired mode       '
        DC      '     then press DONE:                  '
        DC      '      Cancel Erase                     '
        DC      '       Erase All                       '
;
;**************************************************************
;
;       Menu variable definition block
;
```

```
ERASDB:
        DB      3,19,1
        DW      ABLANK
        DB      4,19,1
        DW      ABLANK
        DB      0
;
STMNDB:
OUTDAT: DB      3,13,1
        DW      ABLANK
REDAT:  DB      4,20,1
        DW      ABLANK
ERADAT: DB      3,34,1
        DW      ABLANK
        DB      0
;
MNUODB:                         ;MENU0 variable locations
DESVDB: DB      3,18,1          ;line number,column,characters
        DW      ABLANK          ;pointer to variable,00=dummy pointer
CALVDB: DB      3,35,1
        DW      ABLANK
DATVDB: DB      4,18,1          ;line number,col,number of characters
        DW      ABLANK
DAOVDB: DB      4,35,1
        DW      ABLANK
        DB      0               ;end of VDB
;
DESCDB:
ACTVDB: DB      1,10,10         ;line number,columns,characters
        DW      AACT
FACVDB: DB      2,15,10
        DW      AFAC
PROVDB: DB      3,24,10
        DW      APRO
DAYVDB: DB      4,7,12
        DW      ADATE
        DB      0               ;end of VDB
;
CALIDB:
CALNUM: DB      1+0C0H,12,2     ;bit 7=1, numeric variable
        DW      NCAL            ;bit 6=1, output only numeric variable
CALDEP: DB      1+0C0H,32,3
        DW      IDEPTH
CALSAM: DB      2+80H,09,2      ;line number,column,characters
        DW      NCALS           ;number of calibration samples
CALTLT: DB      2+80H,20,3
        DW      ITILT
CALST:  DB      2,38,1
        DW      ABLANK
CVAL00: DB      3+0C0H,09,3
        DW      CALVAL+0
CVAL01: DB      3+0C0H,13,3
        DW      CALVAL+2
CVAL02: DB      3+0C0H,17,3
        DW      CALVAL+4
CVAL03: DB      3+0C0H,21,3
        DW      CALVAL+6
CVAL04: DB      3+0C0H,25,3
        DW      CALVAL+8
CVAL05: DB      3+0C0H,29,3
        DW      CALVAL+10
CVAL06: DB      3+0C0H,33,3
        DW      CALVAL+12
CVAL07: DB      3+0C0H,37,3
        DW      CALVAL+14
CVAL08: DB      4+0C0H,01,3
        DW      CALVAL+16
CVAL09: DB      4+0C0H,05,3
        DW      CALVAL+18
CVAL10: DB      4+0C0H,09,3
        DW      CALVAL+20
CVAL11: DB      4+0C0H,13,3
        DW      CALVAL+22
CVAL12: DB      4+0C0H,17,3
        DW      CALVAL+24
CVAL13: DB      4+0C0H,21,3
        DW      CALVAL+26
CVAL14: DB      4+0C0H,25,3
        DW      CALVAL+28
CVAL15: DB      4+0C0H,29,3
        DW      CALVAL+30
```

```
CVAL16:  DB      4+0C0H,33,3
         DW      CALVAL+32
CVAL17:  DB      4+0C0H,37,3
         DW      CALVAL+34
         DB      0
;
DAQUDB:
DAQLOC:  DB      1,15,10
         DW      ADAQ
DAQDEP:  DB      1+0C0H,32,3
         DW      IDEPTH
DAQSAM:  DB      2+80H,09,2
         DW      NCALS
DAQTLT:  DB      2+80H,20,3
         DW      ITILT
DAQST:   DB      2,38,1
         DW      ABLANK
DVAL00:  DB      3+0C0H,09,3
         DW      CALVAL+0
DVAL01:  DB      3+0C0H,13,3
         DW      CALVAL+2
DVAL02:  DB      3+0C0H,17,3
         DW      CALVAL+4
DVAL03:  DB      3+0C0H,21,3
         DW      CALVAL+6
DVAL04:  DB      3+0C0H,25,3
         DW      CALVAL+8
DVAL05:  DB      3+0C0H,29,3
         DW      CALVAL+10
DVAL06:  DB      3+0C0H,33,3
         DW      CALVAL+12
DVAL07:  DB      3+0C0H,37,3
         DW      CALVAL+14
DVAL08:  DB      4+0C0H,01,3
         DW      CALVAL+16
DVAL09:  DB      4+0C0H,05,3
         DW      CALVAL+18
DVAL10:  DB      4+0C0H,09,3
         DW      CALVAL+20
DVAL11:  DB      4+0C0H,13,3
         DW      CALVAL+22
DVAL12:  DB      4+0C0H,17,3
         DW      CALVAL+24
DVAL13:  DB      4+0C0H,21,3
         DW      CALVAL+26
DVAL14:  DB      4+0C0H,25,3
         DW      CALVAL+28
DVAL15:  DB      4+0C0H,29,3
         DW      CALVAL+30
DVAL16:  DB      4+0C0H,33,3
         DW      CALVAL+32
DVAL17:  DB      4+0C0H,37,3
         DW      CALVAL+34
         DB      0               ;end of VDB
DATODB:
DATPR:   DB      3,09,1          ;line number,column,characters
         DW      ABLANK
DATCOM:  DB      3,26,1
         DW      ABLANK
DAEXIT:  DB      3,39,1
         DW      ABLANK
         DB      0
;
CRESDB:  DB      1+80H+(01 SHL 3),22,2
         DW      NCAL
         DB      2+80H+(02 SHL 3),23,3
         DW      RMEAN
         DB      3+80H+(03 SHL 3),23,3
         DW      STDDEV
         DB      4+80H+(07 SHL 3),23,3
         DW      NCALS
         DB      0
;
DRESDB:  DB      1+(01 SHL 3),15,10
         DW      ADAQ
         DB      1+80H+(06 SHL 3),34,3
         DW      IDEPTH
         DB      2+80H+(02 SHL 3),15,3
         DW      RMEAN
         DB      2+80H+(04 SHL 3),34,3
         DW      RCORR
```

```
        DB      3+80H+(03 SHL 3),21,3
        DW      STDDEV
        DB      3+80H+(07 SHL 3),34,3
        DW      NCALS
        DB      4+80H+(05 SHL 3),21,5
        DW      STREN
        DB      0
;
ABLANK: DB      ' '             ;a blank ASCII variable
TLTTBL: DC      'Bad '          ;Tilt semaphores
        DC      '+90 '
        DC      '+45 '
        DC      ' 00 '
        DC      '-45 '
        DC      '-90 '
        DC      'NFG '
        DC      'NFG '
;
;*********************************************************************
;                               Key pad code layout
;                               ------TOP------     Special Control Codes:
;       Keypad decoding tables  | 4  3  2  1 |      1==DELETE
;       KEYTBL- unshifted table | 8  7  6  5 |      2==R shift
;       KELTBL- shift left table|12 11 10  9 |      3==M shift
;       KEMTBL- shift middle tab|16 15 14 13 |      4==L shift
;       KERTBL- shift right tab ---BOTTOM----       5==SELECT
;                                                   6==DONE
KEYTBL: DB      001,002,003,004         ;unshifted keypad codes
        DB      005,'3','2','1'
        DB      006,'6','5','4'
        DB      '0','9','8','7'

KELTBL: DB      000,000,000,000         ;shift left keypad codes
        DB      000,'G','D','A'
        DB      000,'P','M','J'
        DB      '+','Y','V','S'
;
KEMTBL: DB      000,000,000,000         ;shift middle keypad codes
        DB      000,'H','E','B'
        DB      000,'Q','N','K'
        DB      '-','Z','W','T'
;
KERTBL: DB      000,00,000,000          ;shift right keypad codes
        DB      000,'I','F','C'
        DB      000,'R','O','L'
        DB      ' ','#','X','U'
;
        END
```

What is claimed is:

1. A measuring apparatus for testing and measuring the compressive strength of an underwater concrete structure, said measuring apparatus comprising:

a housing having a nose at the front end;

a plunger extending from the nose of said housing;

a guide rod mounted within said housing, said guide rod having a spring driven mass mounted thereon, said spring driven mass being in slidable engagement with said guide rod;

the end of said plunger extending from said nose being adapted to engage a surface of said underwater concrete structure so as to allow said measuring apparatus to measure the compressive strength of said structure;

said spring driven mass being released from a locked position and impacting the opposite end of said plunger when said plunger is pressed against the surface of said underwater concrete structure being measured, said spring driven mass rebounding along said guide rod toward the rear of said housing after impacting said plunger;

a resistive film strip mounted within said housing approximately parallel to said guide rod;

an electrically conductive wiper attached to said spring driven mass, said electrically conductive wiper being in slidable engagement with said resistive film strip;

said electrically conductive wiper providing an analog signal proportional to the distance that said spring driven mass rebounds from said plunger after impacting said plunger;

detection circuit means for tracking said analog signal until the peak voltage of said analog signal is reached and then holding the peak voltage of said analog signal;

said detection circuit means providing a status signal indicating that the peak voltage of said analog signal is being held by said detection circuit means; and processing means having a status input and at least three signal inputs, said status input being adapted to receive said status signal from said detection circuit means, said status signal interrupting said processing means so as to allow said processing means to receive at the first signal input thereof the peak voltage of said analog signal and then store the peak voltage of said analog signal;

said processing means calculating the compressive strength of said underwater concrete structure being measured after receiving the peak voltage from at least one test of said structure using said measuring apparatus;

said detection circuit means comprising:

an amplifier circuit for providing a reference voltage;

a voltage comparator having an inverting input for receiving said reference voltage, a noninverting input for receiving said analog signal and an output;

a first inverter having an input connected to the output of said voltage comparator and an output;

an inverting amplifier having an input for receiving said analog signal and an output;

a first peak detector having a first logic input connected to the output of said first inverter, a second logic input connected to the output of said voltage comparator, a signal input connected to the output of said inverting amplifier and a status output;

a voltage source for providing a logic one signal;

a first Flip-Flop having a data input for receiving said logic one signal, a clock input connected to the status output of said first peak detector, a clear input connected to the output of said voltage comparator and a not Q output;

a second inverter having an input connected to the not Q output of said first Flip-Flop and an output;

a NAND gate having a first input connected to the output of said second inverter, a second input and an output;

a third inverter having an input connected to the output of said NAND gate and an output;

a second peak detector having a first logic input connected to the output of said third inverter, a second logic input connected to the not Q output of said first Flip-Flop, a signal input for receiving said analog signal, a signal output connected to the first signal input of said processing means and a status output;

a second Flip-Flop having a data input for receiving said logic one signal, a clock input connected to the status output of said second peak detector, a clear input connected to the not Q output of said first Flip-Flop and a Q output; and a third Flip-Flop having a data input for receiving said logic one signal, a clock input connected to the Q output of said second Flip-Flop and a not Q output connected to the status input of said processing means.

2. The measuring apparatus of claim 1 further comprising a printer electrically coupled to said processing means for providing a report indicative of the compressive strength of said underwater concrete structure being measured.

3. The measuring apparatus of claim 1 further comprising a circuit for providing at least eighteen volts direct current to said measuring apparatus, said circuit comprising:

a receptacle for receiving one hundred twenty volts alternating current, said receptacle having an output;

a line filter having an input connected to the output of said receptacle and an output;

a power supply having an input connected to the output of said line filter and an output, said power supply being adapted to provide approximately twenty-four volts direct current to said measuring apparatus;

a plurality of voltage regulators, each of said voltage regulators having an input connected to the output of said power supply and an output;

a rechargeable battery having an output connected to the inputs of said voltage regulators, said rechargeable battery being adapted to provide approximately eighteen volts direct current to said measuring apparatus;

a momentary contact switch having a first terminal connected to the output of said battery and a second terminal;

a DC to DC converter having an input and an output;

a transistor having an emitter, a base and a collector, said base and said collector being connected to the output of said DC to DC converter and said emitter being connected to the output of one of said voltage regulators;

a zener diode having an anode connected to the base of said transistor and a cathode connected to the inputs of said voltage regulators;

a normally open switch having a pair of normally open contacts, the first normally open contact of said normally open switch being connected between said line filter and said power supply and the second normally open contact of said normally open switch being connected between the output of said battery and the inputs of said voltage regulators;

a resistor connected between the base of said transistor and the output of said DC to DC converter; and a relay having a pair of coils and at least one contact, the fist coil of said relay being connected to the second terminal of said momentary contact switch such that when said momentary contact switch is closed the first coil of said relay is energized closing the contact of said relay to electrically connect the output of said battery to the inputs of said plurality of voltage regulators and the input of said DC to DC converter when the second normally open contact of said normally open switch is closed;

the second coil of said relay being connected to the emitter of said transistor such that when said transistor is turned on the second coil of said relay is energized and the contact of said relay is opened electrically disconnecting said battery from said voltage regulators.

4. The measuring apparatus of claim 4 further comprising battery charger electrically connected to said battery for recharging said battery when the voltage of said battery drops below approximately eighteen volts.

5. The measuring apparatus of claim 4 wherein said rechargeable battery comprises a lead acid battery.

6. The measuring apparatus of claim 1 further comprising a pressure transducer having an output connected to the second signal input of said processing means.

7. The measuring apparatus of claim 1 further comprising keypad means for entering data into said processing means via the third signal input of said processing means.

8. The measuring apparatus of claim 7 further comprising an encoder electrically connected between said keypad means and the third signal input of said processing means.

9. The measuring apparatus of claim 1 further comprising a ten volt power supply electrically connected to said resistive strip for providing to said resistive strip a direct current voltage.

10. A measuring apparatus for testing and measuring the compressive strength of an underwater concrete structure, said measuring apparatus comprising:

a housing having a nose at the front end;

a plunger extending from the nose of said housing;

a guide rod mounted within said housing, said guide rod having a spring driven mass mounted thereon, said spring driven mass being in slidable engagement with said guide rod;

the end of said plunger extending from said nose being adapted to engage a surface of said underwater concrete structure so as to allow said measuring apparatus to measure the compressive strength of said structure;

said spring driven mass being released from a locked position and impacting the opposite end of said plunger when said plunger is pressed against the surface of said underwater concrete structure being measured, said spring driven mass rebounding along said guide rod toward the rear of said housing after impacting said plunger;

a resistive film strip mounted within said housing approximately parallel to said guide rod;

an electrically conductive wiper attached to said spring driven mass, said electrically conductive wiper being in slidable engagement with said resistive film strip;

said electrically conductive wiper providing an analog signal proportional to the distance that said spring driven mass rebounds from said plunger after impacting said plunger;

first power supplying means for providing a first direct current voltage to said resistive strip so as to allow said electrically conductive wiper to provide said analog signal;

detection circuit means for tracking said analog signal until the peak voltage of said analog signal is reached and then holding the peak voltage of said analog signal;

said detection circuit means providing a status signal indicating that the peak voltage of said analog signal is being held by said detection circuit means;

processing means having a status input and at least three signal inputs, said status input being adapted to receive said status signal from said detection circuit means, said status signal interrupting said processing means so as to allow said processing means to receive at the first signal input thereof the peak voltage of said analog signal and then store the peak voltage of said analog signal;

said processing means calculating the compressive strength of said underwater concrete structure being measured after receiving the peak voltage from at least one test of said structure using said measuring apparatus;

second power supply means for providing a second direct current voltage to said first power supplying means, said processing means and said detection circuit means;

said second power supplying means including a self contained rechargeable battery, said rechargeable battery having an output electrically connected to said first power supplying means, said processing means and said detection circuit means; and sensing circuit means for disconnecting said rechargeable battery from said first power supplying means, said processing means and said detection circuit means when said battery discharges below a predetermined voltage;

said detection circuit means comprising:

an amplifier circuit for providing a reference voltage;

a voltage comparator having an inverting input for receiving said reference voltage, a noninverting input for receiving said analog signal and an output;

a first inverter having an input connected to the output of said voltage comparator and an output;

an inverting amplifier having an input for receiving said analog signal and an output;

a first peak detector having a first logic input connected to the output of said first inverter, a second logic input connected to the output of said voltage comparator, a signal input connected to the output of said inverting amplifier and a status output;

a voltage source for providing a logic one signal;

a first Flip-Flop having a data input for receiving said logic one signal, a clock input connected to the status output of said first peak detector, a clear input connected to the output of said voltage comparator and a not Q output;

a second inverter having an input connected to the not Q output of said first Flip-Flop and an output;

A NAND gate having a first input connected to the output of said second inverter, a second input and an output;

a third inverter having an input connected to the output of said NAND gate and an output;

a second peak detector having a first logic input connected to the output of said third inverter, a second logic input connected to the not Q output of said first Flip-Flop, a signal input for receiving said analog signal, a signal output connected to the first signal input of said processing means and a status output;

a second Flip-Flop having a data input for receiving said logic one signal, a clock input connected to the status output of said second peak detector, a clear input connected to the not Q output of said first Flip-Flop and a Q output; and a third Flip-Flop having a data input for receiving said logic one signal, a clock input connected to the Q output of said second Flip-Flop and a not Q output connected to the status input of said processing means.

11. The measuring apparatus of claim 10 wherein said sensing circuit means comprises:

a momentary contact switch having a first terminal connected to the output of said rechargeable battery and a second terminal;

a DC to DC converter having an input and an output;

a direct current voltage source having an output;

a transistor having an emitter, a base and a collector, said base and said collector being connected to the output of said DC to DC converter and said emitter being connected to direct current voltage source;

a zener diode having an anode connected to the base of said transistor and a cathode connected to said first power supplying means;

a normally open switch having at least one normally open contact, the normally open contact of said normally open switch electrically connecting the output of said rechargeable battery to said first power supply means, said processing means and said detection circuit means when said normally open switch is closed;

a resistor connected between the base of said transistor and the output of said DC to DC converter; and a relay having a pair of coils and at least one contact, the first coil of said relay being connected to the second terminal of said momentary contact switch such that when said momentary contact switch is closed said coil is energized closing the contact of said relay to electrically connect said rechargeable battery to said first power supplying means, said processing means and said detection circuit means when said normally open switch is closed;

the second coil of said relay being connected to the emitter of said transistor such that when said transistor is turned on the second coil of said relay is energized and the contact of said relay is opened electrically disconnecting said rechargeable battery from said first power supplying means, said microprocessing means and said detection circuit means.

12. The measuring apparatus of claim 10 further comprising a printer electrically coupled to said processing means for providing a report indicative of the compressive strength of said underwater concrete structure being measured.

13. The measuring apparatus of claim 10 further comprising a battery charger electrically connected to said rechargeable battery for recharging said rechargeable battery when the voltage of said rechargeable battery drops below said predetermined voltage.

14. The measuring apparatus of claim 10 wherein said rechargeable battery comprises a lead acid battery.

15. The measuring apparatus of claim 10 further comprising a pressure transducer having an output connected to the second signal input of said processing means.

16. The measuring apparatus of claim 10 further comprising keypad means for entering data into said processing means via the third signal input of said processing means.

17. The measuring apparatus of claim 16 further comprising an encoder electrically connected between said keypad means and the third signal input of said processing means.

18. The measuring apparatus of claim 10 wherein said first power supplying means is a ten volt power supply electrically connected to said resistive strip for providing said resistive strip and said first direct current voltage.

* * * * *